US010385263B2

(12) United States Patent
Fuchs et al.

(10) Patent No.: US 10,385,263 B2
(45) Date of Patent: Aug. 20, 2019

(54) HETEROLEPTIC TRANSITION METAL-CARBENE COMPLEXES AND THEIR USE IN ORGANIC LIGHT-EMITTING DIODES (OLEDS)

(75) Inventors: Evelyn Fuchs, Mannheim (DE);
Martina Egen, Dossenheim (DE);
Klaus Kahle, Ludwigshafen (DE);
Christian Lennartz, Schifferstadt (DE);
Oliver Molt, Hirschberg (DE); Simon Nord, Roemerberg (DE); Wolfgang Kowalsky, Braunschweig (DE);
Christian Schildknecht, Dannstadt-Schauernheim (DE);
Hans-Hermann Johannes, Braunschweig (DE)

(73) Assignee: UDC IRELAND LIMITED, Dublin (IE)

( * ) Notice: Subject to any disclaimer, the term of this patent is extended or adjusted under 35 U.S.C. 154(b) by 1103 days.

(21) Appl. No.: 12/296,112

(22) PCT Filed: Apr. 3, 2007

(86) PCT No.: PCT/EP2007/053213
§ 371 (c)(1),
(2), (4) Date: Oct. 6, 2008

(87) PCT Pub. No.: WO2007/115970
PCT Pub. Date: Oct. 18, 2007

(65) Prior Publication Data
US 2009/0096367 A1 Apr. 16, 2009

(30) Foreign Application Priority Data
Apr. 5, 2006 (EP) .................................. 06112228

(51) Int. Cl.
| H01L 51/54 | (2006.01) |
| C09K 11/06 | (2006.01) |
| C07F 15/00 | (2006.01) |
| H01L 51/00 | (2006.01) |
| H05B 33/14 | (2006.01) |
| H01L 51/50 | (2006.01) |

(52) U.S. Cl.
CPC .......... *C09K 11/06* (2013.01); *C07F 15/0033* (2013.01); *H01L 51/0085* (2013.01); *H05B 33/14* (2013.01); *C09K 2211/1007* (2013.01); *C09K 2211/1044* (2013.01); *C09K 2211/1059* (2013.01); *C09K 2211/185* (2013.01); *H01L 51/005* (2013.01); *H01L 51/0059* (2013.01); *H01L 51/5012* (2013.01); *H01L 51/5016* (2013.01)

(58) Field of Classification Search
CPC ... H01L 51/0083–0089; H01L 51/0091; H01L 51/0092; H01L 51/5016; C09K 11/06; C09K 2211/1029–1085; C09K 11/181–187; C07F 15/0006; C07F 15/002; C07F 15/0033; C07F 15/0046; C07F 15/006; C07F 15/0073; C07F 15/0086; C07F 15/02; C07F 15/04; C07F 15/06

See application file for complete search history.

(56) References Cited

U.S. PATENT DOCUMENTS

| 2005/0258433 | A1* | 11/2005 | Djurovich et al. ........................ H01L 51/0067 257/79 |
| 2006/0258043 | A1 | 11/2006 | Bold et al. |
| 2007/0282076 | A1 | 12/2007 | Bold et al. |
| 2008/0018221 | A1* | 1/2008 | Egen et al. ............ C09K 11/06 313/483 |
| 2010/0213834 | A1 | 8/2010 | Molt et al. |

FOREIGN PATENT DOCUMENTS

| DE | 102004057072 A1 * | 6/2006 |
| DE | 102005014284 A1 * | 9/2006 |
| WO | 2005 019373 | 3/2005 |
| WO | 2005 113704 | 12/2005 |
| WO | 2006 018292 | 2/2006 |

OTHER PUBLICATIONS

U.S. Appl. No. 12/597,651, filed Oct. 26, 2009, US 2010/0187980 A1, Moonen, et al.

* cited by examiner

Primary Examiner — Marie R. Yamnitzky
(74) Attorney, Agent, or Firm — Riverside Law LLP

(57) ABSTRACT

The present invention relates to heteroleptic carbene complexes comprising at least two different carbene ligands, to a process for preparing the heteroleptic carbene complexes, to the use of the heteroleptic carbene complexes in organic light-emitting diodes, to organic light-emitting diodes comprising at least one inventive heteroleptic carbene complex, to a light-emitting layer comprising at least one inventive heteroleptic carbene complex, to organic light-emitting diodes comprising at least one inventive light-emitting layer, and to devices which comprise at least one inventive organic light-emitting diode.

17 Claims, No Drawings

HETEROLEPTIC TRANSITION METAL-CARBENE COMPLEXES AND THEIR USE IN ORGANIC LIGHT-EMITTING DIODES (OLEDS)

The present invention relates to heteroleptic carbene complexes comprising at least two different carbene ligands, to a process for preparing the heteroleptic carbene complexes, to the use of the heteroleptic carbene complexes in organic light-emitting diodes, to organic light-emitting diodes comprising at least one inventive heteroleptic carbene complex, to a light-emitting layer comprising at least one inventive heteroleptic carbene complex, to organic light-emitting diodes comprising at least one inventive light-emitting layer, and to devices which comprise at least one inventive organic light-emitting diode.

In organic light-emitting diodes (OLEDs), the property of materials to emit light when they are excited by electrical current is exploited. OLEDs are of interest especially as an alternative to cathode ray tubes and liquid-crystal displays for the production of flat visual display units. Owing to the very compact design and the intrinsically low electricity consumption, the devices comprising OLEDs are especially suitable for mobile applications, for example for uses in cell phones, laptops, etc.

The basic principles of the functioning of OLEDs and suitable assemblies (layers) of OLEDs are specified, for example, in WO 2005/113704 and the literature cited therein.

The prior art has already proposed numerous materials which emit light on excitation by electrical current.

WO 2005/019373 for the first time discloses the use of uncharged transition metal complexes which comprise at least one carbene ligand in OLEDs. According to WO 2005/019373, these transition metal complexes can be used in any layer of an OLED, the ligand structure or central metal being variable for adjustment to the desired properties of the transition metal complexes. For example, the use of the transition metal complexes in a blocking layer for electrons, a blocking layer for excitons, a blocking layer for holes, or the light-emitting layer of the OLED is possible, preference being given to using the transition metal complexes as emitter molecules in OLEDs.

WO 2005/113704 relates to luminescent compounds which bear carbene ligands. WO 2005/113704 specifies numerous transition metal complexes with different carbene ligands, preference being given to using the transition metal complexes as phosphorescent light-emitting material, more preferably as a doping substance.

Even though compounds suitable for use in OLEDs, especially as light-emitting substances, are already known, the provision of more efficient compounds which are useable industrially is desirable. In the context of the present application, the electroluminescence refers both to electrofluorescence and to electrophosphorescence.

It is therefore an object of the present application to provide novel carbene complexes which are suitable for use in OLEDs. In particular, the provision of transition metal complexes which exhibit electroluminescence with good efficiencies is desirable. Furthermore, the novel carbene complexes shall enable "color fine-tuning" with simultaneously good efficiency.

This object is achieved by the provision of heteroleptic carbene complexes of the general formula (I)

(I)  $M^1[\text{carbene}]_n$ comprising at least two different carbene ligands,
in which the symbols are each defined as follows:
$M^1$ is a metal atom selected from the group consisting of Ir, Co, Rh, Ni, Pd, Pt, Fe, Ru, Os, Cr, Mo, W, Mn, Tc, Re, Cu and Au, preferably Ir, Os, Ru, Rh, Pd, Co and Pt, more preferably Ir, Pt, Rh and Os, in any oxidation state possible for the corresponding metal atom;
n is the number of carbene ligands, where n is at least 2; where n is dependent on the oxidation state and coordination number of the metal atom used and on the denticity and on the charge of the carbene ligands;
carbene is a carbene ligand of the general formula (II)

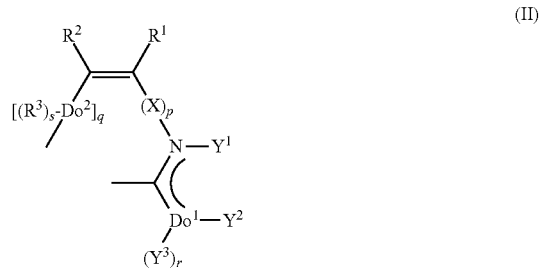

where the symbols in the carbene ligand of the general formula II are each defined as follows:
$Do^1$ is a donor atom selected from the group consisting of C, P, N, O, S and Si, preferably P, N, O and S;
$Do^2$ is a donor atom selected from the group consisting of C, N, P, O and S;
r is 2 when $Do^1$ is C or Si, is 1 when $Do^1$ is N or P, and is 0 when $Do^1$ is O or S;
s is 2 when $Do^2$ is C, is 1 when $Do^2$ is N or P, and is 0 when $Do^2$ is O or S;
X is a spacer selected from the group consisting of silylene, alkylene, arylene, heteroarylene, alkynylene, alkenylene, $NR^{13}$, $PR^{14}$, $BR^{15}$, O, S, SO, $SO_2$, CO, CO—O, O—CO and $(CR^{16}R^{17})_w$, where one or more nonadjacent $(CR^{16}R^{17})$ groups may be replaced by $NR^{13}$, $PR^{14}$, $BR^{15}$, O, S, SO, $SO_2$, CO, CO—O, O—CO;
w is from 2 to 10;
$R^{13}$, $R^{14}$, $R^{15}$, $R^{16}$, $R^{17}$ are each H, alkyl, aryl, heteroaryl, alkenyl, alkynyl;
p is 0 or 1;
q is 0 or 1;
$Y^1$, $Y^2$ are each independently hydrogen or a carbon group selected from the group consisting of alkyl, aryl, heteroaryl, alkynyl and alkenyl groups;
or
$Y^1$ and $Y^2$ together form a bridge between the donor atom $Do^1$ and the nitrogen atom N, said bridge having at least two atoms of which at least one is a carbon atom,
$R^1$, $R^2$ are each independently hydrogen, alkyl, aryl, heteroaryl, alkynyl or alkenyl radicals,
or
$R^1$ and $R^2$ together form a bridge having a total of from three to five atoms, of which from 1 to 5 atoms may be heteroatoms and the remaining atoms are carbon atoms, so that the group

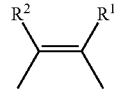

forms a five- to seven-membered ring which, if appropriate—in addition to the double bond already present—may have one further double bond or—in the case of a six- or seven-membered ring—two further double bonds, and may optionally be substituted by alkyl or aryl groups and/or groups with donor or acceptor action, and may optionally comprise at least one heteroatom, and the five- to seven-membered ring may optionally be fused to one or more further rings, preferably six-membered aromatic rings;

in addition, $Y^1$ and $R^1$ may be bonded to one another via a bridge, where the bridge may be defined as follows:
alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where
x is from 2 to 10;
and
$R^{18}$, $R^{19}$, $R^{20}$, $R^{21}$, $R^{22}$, $R^{30}$, $R^{31}$
are each H, alkyl, aryl, heteroaryl, alkenyl, alkynyl;
$R^3$ is hydrogen, an alkyl, aryl, heteroaryl, alkynyl or alkenyl radical;
wherein the at least 2 carbene ligands have different definitions of $Y^3$, where
$Y^3$ in at least one first carbene ligand (IIa) is defined as follows:
hydrogen, an alkyl, alkynyl or alkenyl radical,
where, when $Do^1$ is C or Si and r is 2, the two $Y^3$ radicals are each as defined above;
and
$Y^3$ in at least one second carbene ligand (IIb) is defined as follows:

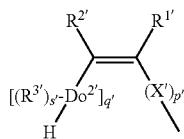

where $Do^{2'}$, q', s', $R^{3'}$, $R^{1'}$, $R^{2'}$, X' and p' are each independently as defined for $Do^2$, q, s, $R^3$, $R^1$, $R^2$, X and p, and when $Do^1$ is C or Si and r is 2, at least one of the two $Y^3$ radicals is as defined above; the second $Y^3$ radical may be as defined above or be defined as specified for $Y^3$ with regard to the first carbene ligand;
and
$Y^3$ in a third or further carbene ligand in heteroleptic carbene complexes of the general formula I in which n is >2 is either as defined in the first carbene ligand (IIa) or as defined in the second carbene ligand (IIb);
in addition, $Y^3$ and $Y^2$ in each of the n carbene ligands may be bonded to one another via a bridge, where the bridge may be defined as follows:
alkylene, arylene, heteroarylene, alkynylene, alkenylene, $NR^{25}$, $PR^{26}$, $BR^{27}$, O, S, SO, $SO_2$, $SiR^{32}R^{33}$, CO, CO—O, O—CO and $(CR^{28}R^{29})_y$, where one or more nonadjacent $(CR^{28}R^{29})$ groups may be replaced by $NR^{25}$, $PR^{26}$, $BR^{27}$, O, S, SO, $SO_2$, $SiR^{32}R^{33}$, CO, CO—O, O—CO, where
y is from 2 to 10;
and
$R^{25}$, $R^{26}$, $R^{27}$, $R^{28}$, $R^{29}$, $R^{32}$, $R^{33}$
are each H, alkyl, aryl, heteroaryl, alkenyl, alkynyl.

In the case that $Do^1$ is O or S, the carbene ligand of the general formula II is thus an unsymmetrical carbene ligand in the context of the present application.

The inventive heteroleptic carbene complexes of the formula I are thus notable in that they have at least two different carbene ligands (at least one first carbene ligand IIa and at least one second carbene ligand IIb). Depending on the oxidation state and coordination number of the metal atom $M^1$ used and on the denticity and on the charge of the carbene ligands, further carbene ligands may be present in the inventive heteroleptic carbene complex as well as the first carbene ligand IIa and the second carbene ligand IIb. The structure of these carbene ligands may correspond either to the structure of the first carbene ligand IIa or to the structure of the second carbene ligand IIb, where the substitution patterns of the individual carbene ligands may be different.

The first carbene ligand IIa is also referred to hereinafter as "unsymmetrical carbene ligand", while the second carbene ligand IIb is referred to as "symmetrical carbene ligand". In the context of the present application, a symmetrical carbene ligand should not be understood to mean that the substituent $Y^3$ must be identical to the group bonded to the nitrogen atom of the carbene ligand shown in the general formula II, or that $Do^1$ must be N, and/or $Y^1$ and $Y^2$ must be identical or together must form an exactly symmetrical radical. The substitution patterns of the individual groups may quite possibly be different.

In the context of the present application, a symmetrical carbene ligand is understood to mean a carbene ligand in which the base structure of the substituent $Y^3$ corresponds to the base structure of the group bonded to the nitrogen atom in the carbene ligand of the general formula II, where the substitution patterns of the groups may be different.

It has been found that the inventive heteroleptic carbene complexes which comprise at least one symmetrical carbene ligand (second carbene ligand IIb) and at least one unsymmetrical carbene ligand (first carbene ligand IIa), compared to corresponding complexes which have identical carbene ligands, are notable in that the different ligands (symmetrical and unsymmetrical carbene ligands in one carbene complex) can achieve fine adjustment of the emission color, i.e. a mixture of the colors of the corresponding pure carbene complexes with only one type of ligand in each case, the photoluminescence quantum yields of the mixed complexes surprisingly not being between the quantum yields of the pure complexes but rather just as high as in the more efficient of the pure complexes. It has thus been found that, surprisingly, the inventive heteroleptic carbene complexes of the general formula I allow the emission color to be adjusted without a deterioration in the quantum yield in the direction of the quantum yield of the less efficient complex.

Depending on the coordination number of the metal $M^1$ used and the number of carbene ligands and non-carbene ligands used, different isomers of the corresponding metal complexes may be present for the same metal $M^1$ and the same nature of the carbene ligands and non-carbene ligands used. For example, in the case of complexes with a metal $M^1$ of coordination number 6 (i.e. octahedral complexes), for example Ir(III) complexes, "fac-mer isomers" (facial/meridional isomers) are possible when the complexes are of the general composition $M(AB)_2(CD)$ where AB and CD are bidentate ligands. In the context of the present application, "fac-mer isomers" refer to the isomers shown below:

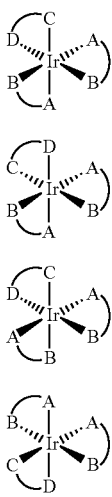

fac-isomer 1 fac-isomer 2 mer-isomer 3 mer-isomer 4

In square-planar complexes with a metal $M^1$ of coordination number 4, for example Pt(II) complexes, "isomers" are possible when the complexes are of the general composition M(AB)(CD) where AB and CD are bidentate ligands. In the context of the present application, "isomers" are understood to mean the isomers shown below:

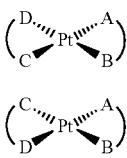

isomer 1 isomer 2

The symbols A and B, and C and D, are each one binding site of a ligand, only bidentate ligands being present. According to the aforementioned general composition, a bidentate ligand has an A group and a B group, or a C group and a D group.

It is known in principle to those skilled in the art what is meant by cis/trans and fac-mer isomers. In complexes of the composition $MA_3B_3$, three groups of the same type can either occupy the corners of an octahedral face (facial isomer) or a meridian, i.e. two of the three ligand binding sites are trans relative to one another (meridional isomer). With regard to the definition of cis/trans isomers and fac-mer isomers in octahedral metal complexes, see, for example, J. Huheey, E. Keiter, R. Keiter, Anorganische Chemie: Prinzipien von Struktur und Reaktivität [Inorganic chemistry: Principles of Structure and Reactivity], 2nd, newly revised edition, translated into German and expanded by Ralf Steudel, Berlin; New York: de Gruyter, 1995, pages 575, 576.

In square-planar complexes, cis isomerism means that, in complexes of the composition $MA_2B_2$, both the two A groups and the two B groups occupy adjacent corners of a square, while both the two A groups and the two B groups in trans isomerism each occupy the two mutually diagonal corners of a square. With regard to the definition of cis/trans isomers in square-planar metal complexes, see, for example, J. Huheey, E. Keiter, R. Keiter, Anorganische Chemie: Prinzipien von Struktur und Reaktivität, 2nd, newly revised edition, translated into German and expanded by Ralf Steudel, Berlin; New York: de Gruyter, 1995, pages 557 to 559.

In general, the different isomers of the metal complexes of the formula I can be separated by processes known to those skilled in the art, for example by chromatography, sublimation or crystallization.

The present invention therefore relates in each case both to the individual isomers of the carbene complexes of the formula I and to mixtures of different isomers in any mixing ratio.

The inventive heteroleptic carbene complexes of the general formula I more preferably have a metal atom $M^1$ selected from the group consisting of Ir, Os, Rh and Pt, preference being given to Os(II), Rh(III), Ir(III) and Pt(II). Particular preference is given to Ir(III).

The number n of carbene ligands of the general formula II in the inventive heteroleptic carbene complexes of the formula I in which the transition metal atom Ir(III) has a coordination number of 6 is generally 3, i.e. a first (unsymmetrical) carbene ligand (IIa), a second (symmetrical) carbene ligand (IIb) and a third carbene ligand of the general formula II which is either symmetrical or unsymmetrical.

The number n of carbene ligands in transition metal complexes in which the transition metal atom Pt(II) has a coordination number of 4 is 2, i.e. a first (unsymmetrical) carbene ligand (IIa), a second (symmetrical) carbene ligand (IIb).

For the $Y^1$ and $Y^2$ groups, in the context of the present application (both for symmetrical and for unsymmetrical carbene ligands):

the substituents of the $Y^1$ and $Y^2$ groups may together form a bridge having a total of from two to four, preferably from two to three, atoms, of which one or two atoms may be heteroatoms, preferably N, and the remaining atoms are carbon atoms, so that the $NCDo^1$ moiety, together with this bridge, form a five- to seven-membered, preferably five- to six-membered, ring which may optionally have two or—in the case of a six- or seven-membered ring—three double bonds and may optionally be substituted by alkyl or aryl groups and/or groups with donor or acceptor action, and may optionally comprise heteroatoms, preferably N, preference being given to a five-membered or six-membered aromatic ring which is substituted by alkyl or aryl groups and/or groups with donor or acceptor action or is unsubstituted, or the preferred five-membered or six-membered aromatic ring is fused to further rings which may optionally comprise at least one heteroatom, preferably N, preferably six-membered aromatic rings.

The $Y^1$ group may be bonded to the $R^1$ radical via a bridge, where the bridge may be defined as follows:
Alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;
and
$R^{18}$, $R^{19}$, $R^{20}$, $R^{21}$, $R^{22}$, $R^{30}$, $R^{31}$
are each H, alkyl, aryl, heteroaryl, alkenyl, alkynyl.

In the case that $Y^1$ and $Y^2$ together form a bridge to form a five- to seven-membered ring, the bridge which bonds it to the $R^1$ radical may be bonded directly to the five- to seven-membered ring or be bonded to a substituent of this ring, preference being given to a direct bond to the five- to seven-membered ring. The atom directly adjacent to the nitrogen atom (in the general formula II) of the five- to seven-membered ring is more preferably bonded to $R^1$ via a bridge when such a bond is present (see, for example, the bridged structures hereinafter). In the case that the five- to seven-membered ring formed by a common bridge of $Y^1$ and $Y^2$ is fused to a further five- to seven-membered ring, the joining bridge can be bonded to an atom of the fused ring (see, for example, the bridged structures hereinafter).

Preferred bridged structures are specified hereinafter by way of example for symmetrical and unsymmetrical carbene ligands. The groups shown in the ligand systems shown may, for example, bear substituents, or one or more CH groups in the aromatic groups shown may be replaced by heteroatoms. It is likewise possible that the carbene ligands have a plurality of identical or different bridges. The bridges shown may also occur in other ligand systems used in accordance with the invention, for example in the ligand systems of the formulae IIaa to IIae and IIba to IIbe mentioned below.

Examples of unsymmetrical carbene ligands with bridged structures:

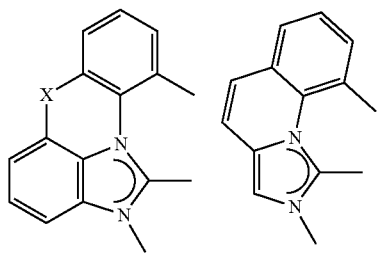

X = O, S, SO, $SO_2$,
$CH_2$ $CMe_2$, $SiR^{30}R^{31}$, NMe

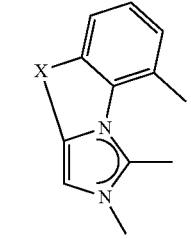

X = O, S, SO, $SO_2$,
$CH_2$, $CMe_2$, $SiR^{30}R^{31}$, NMe

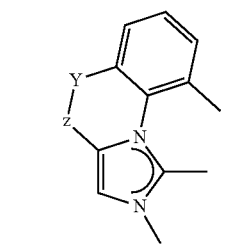

Y-Z = 1x $CR^{21}R^{22}$ and 1x O, S,
SO, $SO_2$, $CR^{21}R^{22}$, $SiR^{30}R^{31}$, $NR^{18}$
or Y-Z = CO—O, O—CO Examples of symmetrical carbene ligands with bridged structures:

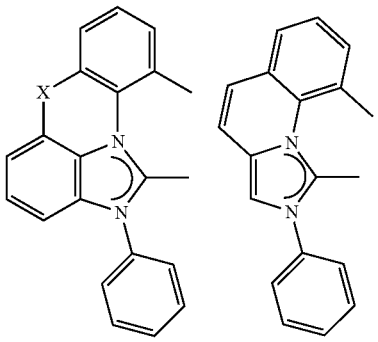

X = O, S, SO, $SO_2$,
$CH_2$ $CMe_2$, $SiR^{30}R^{31}$, NMe

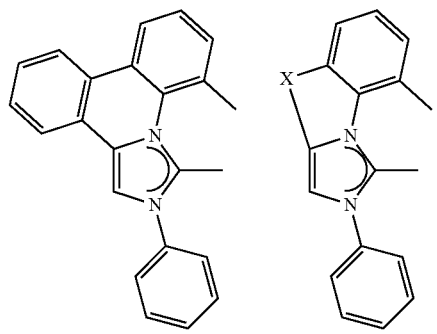

X = O, S, SO, $SO_2$,
$CH_2$, $CMe_2$, $SiR^{30}R^{31}$, NMe

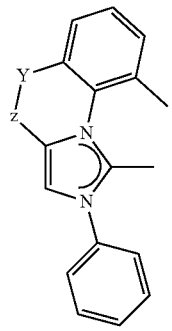

Y-Z = 1x $CR^{21}R^{22}$ and 1x O, S,
SO, $SO_2$, $CR^{21}R^{22}$, $SiR^{30}R^{31}$, $NR^{18}$
or Y-Z = CO—O, O—CO

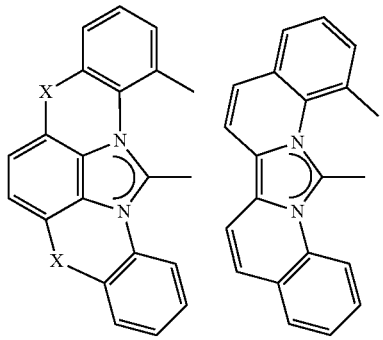

X = O, S, SO, $SO_2$,
$CH_2$, $CMe_2$, $SiR^{30}R^{31}$, NMe

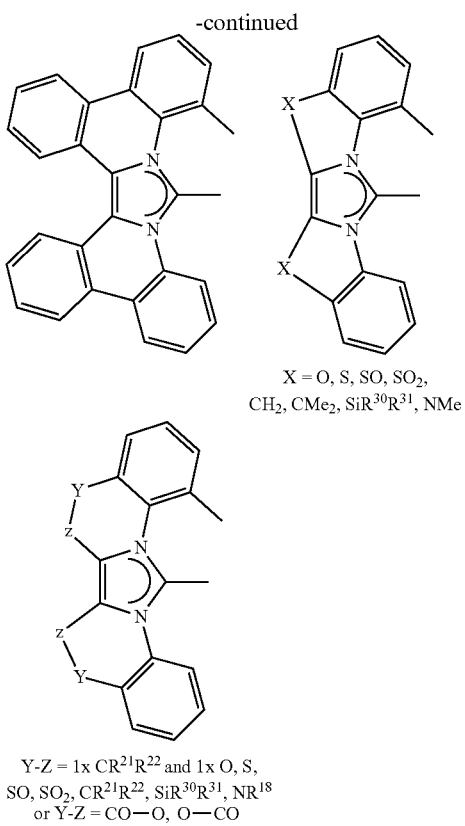

X = O, S, SO, SO$_2$,
CH$_2$, CMe$_2$, SiR$^{30}$R$^{31}$, NMe

Y-Z = 1x CR$^{21}$R$^{22}$ and 1x O, S,
SO, SO$_2$, CR$^{21}$R$^{22}$, SiR$^{30}$R$^{31}$, NR$^{18}$
or Y-Z = CO—O, O—CO The R$^{18}$, R$^{21}$, R$^{22}$, R$^{30}$ and R$^{31}$ radicals have already been defined above.

In the context of the present application, the terms aryl radical or group, heteroaryl radical or group, alkyl radical or group, and alkenyl radical or group, and alkynyl radical or group are each defined as follows:

An aryl radical (or group) is understood to mean a radical with a base structure of from 6 to 30 carbon atoms, preferably from 6 to 18 carbon atoms, which is formed from an aromatic ring or a plurality of fused aromatic rings. Suitable base structures are, for example, phenyl, naphthyl, anthracenyl or phenanthrenyl. This base structure may be unsubstituted (i.e. all carbon atoms which are substitutable bear hydrogen atoms) or be substituted at one, more than one or all substitutable positions of the base structure. Suitable substituents are, for example, alkyl radicals, preferably alkyl radicals having from 1 to 8 carbon atoms, more preferably methyl, ethyl or i-propyl, aryl radicals, preferably C$_6$-aryl radicals, which may in turn be substituted or unsubstituted, heteroaryl radicals, preferably heteroaryl radicals which comprise at least one nitrogen atom, more preferably pyridyl radicals, alkenyl radicals, preferably alkenyl radicals which bear a double bond, more preferably alkenyl radicals having a double bond and from 1 to 8 carbon atoms, or groups with donor or acceptor action. Suitable groups with donor or acceptor action are specified below. Most preferably, the aryl radicals bear substituents selected from the group consisting of methyl, F, Cl, CN, aryloxy and alkoxy, sulfonyl, heteroaryl. The aryl radical or the aryl group is preferably a C$_6$-C$_{18}$-aryl radical, more preferably a C$_6$-aryl radical, which is optionally substituted by at least one of the aforementioned substituents. The C$_6$-C$_{18}$-aryl radical, preferably C$_6$-aryl radical, more preferably has one or two of the aforementioned substituents, where, in the case of a C$_6$-aryl radical, one substituent may be arranged in the ortho, meta or para position to the further bonding site of the aryl radical, and—in the case of two substituents—they may each be arranged in the meta position or ortho position to the further bonding site of the aryl radical, or one radical is arranged in the ortho position and one radical in the meta position, or one radical is arranged in the ortho or meta position and the further radical is arranged in the para position.

A heteroaryl radical or a heteroaryl group is understood to mean radicals which differ from the aforementioned aryl radicals in that at least one carbon atom in the base structure of the aryl radicals is replaced by a heteroatom. Preferred heteroatoms are N, O and S. Most preferably, one or two carbon atoms of the base structure of the aryl radicals are replaced by heteroatoms. Especially preferably, the base structure is selected from systems such as pyridine and five-membered heteroaromatics such as pyrrole, furan, pyrazole, imidazole, thiophene, oxazole, thiazole. The base structure may be substituted at one, more than one or all substitutable positions of the base structure. Suitable substituents are the same as have already been mentioned for the aryl groups.

An alkyl radical or an alkyl group is understood to mean a radical having from 1 to 20 carbon atoms, preferably from 1 to 10 carbon atoms, more preferably from 1 to 8 carbon atoms. This alkyl radical may be branched or unbranched and optionally be interrupted by one or more heteroatoms, preferably Si, N, O or S, more preferably N, O or S. In addition, this alkyl radical may be substituted by one or more of the substituents mentioned for the aryl groups. It is likewise possible that the alkyl radical bears one or more (hetero)aryl groups. In this context, all of the (hetero)aryl groups listed above are suitable. The alkyl radicals are more preferably selected from the group consisting of methyl, ethyl, isopropyl, n-propyl, n-butyl, isobutyl and tert-butyl; very particular preference is given to methyl and isopropyl.

An alkenyl radical or an alkenyl group is understood to mean a radical which corresponds to the aforementioned alkyl radicals having at least two carbon atoms, with the difference that at least one C—C single bond of the alkyl radical has been replaced by a C—C double bond. The alkenyl radical preferably has one or two double bonds.

An alkynyl radical or an alkynyl group is understood to mean a radical which corresponds to the aforementioned alkyl radicals having at least two carbon atoms, with the difference that at least one C—C single bond of the alkyl radical has been replaced by a C—C triple bond. The alkynyl radical preferably has one or two triple bonds.

In the context of the present application, the terms alkylene, arylene, heteroarylene, alkynylene and alkenylene are each as defined for the alkyl, aryl, heteroaryl, alkynyl and alkenyl radicals, with the difference that the alkylene, arylene, heteroarylene, alkynylene and alkenylene groups each have two binding sites to atoms of the ligand of the formula II.

A bridge which is formed from Y$^1$ and Y$^2$ and has at least two atoms, of which at least one is a carbon atom, and the further atoms are preferably nitrogen or carbon atoms, where the bridge may be saturated or preferably unsaturated and the at least two atoms of the bridge may be substituted or unsubstituted, is preferably understood to mean the following groups:

A bridge which has two carbon atoms or one carbon atom and one nitrogen atom, where the carbon atoms or one carbon atom and one nitrogen atom are bonded to one another by a double bond, so that the bridge has one of the following formulae, where the bridge preferably has two carbon atoms:

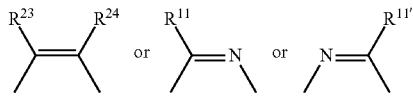

$R^{23}$, $R^{24}$, $R^{11}$ and $R^{11'}$ are each independently hydrogen, alkyl, heteroaryl, alkenyl, alkynyl, aryl or a substituent with donor or acceptor action, or $R^{23}$ and $R^{24}$ together form a bridge having a total of from 3 to 5, preferably 4, atoms, of which from 1 to 5 may optionally be heteroatoms, preferably N, and the remaining atoms are carbon atoms, so that this group forms a 5- to 7-membered, preferably six-membered, ring which optionally—in addition to the double bond already present—may have one further double bond or—in the case of a six- or seven-membered ring—may have two further double bonds, and may optionally be substituted by alkyl or aryl groups and/or groups with donor or acceptor action. Preference is given to a six-membered aromatic ring. This may be substituted by alkyl or aryl groups and/or groups with donor or acceptor action, or be unsubstituted. In addition, it is possible that one or more further aromatic rings are fused to this preferably six-membered aromatic ring. In this context, any conceivable fusion is possible. These fused radicals may in turn be substituted, preferably by the radicals specified in the general definition of the aryl radicals.

A bridge which has two carbon atoms, where the carbon atoms are bonded to one another by a single bond, so that the bridge has the following formula:

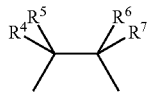

in which $R^4$, $R^5$, $R^6$ and $R^7$ are each independently hydrogen, alkyl, heteroaryl, alkenyl, alkynyl, aryl or a substituent with donor or acceptor action, preferably hydrogen, alkyl or aryl.

In the context of the present application, a group or a substituent having donor or acceptor action is understood to mean the following groups:

Groups with donor action are understood to mean groups which have a +I and/or +M effect, and groups with acceptor action are understood to mean groups which have a −I and/or −M effect. Suitable groups with donor or acceptor action are halogen radicals, preferably F, Cl, Br, more preferably F, alkoxy radicals, aryloxy radicals, carbonyl radicals, ester radicals, both oxycarbonyl and carbonyloxy, amine radicals, amide radicals, $CH_2F$ groups, $CHF_2$ groups, $CF_3$ groups, CN groups, thio groups, sulfonic acid groups, sulfonic ester groups, boronic acid groups, boronic ester groups, phosphonic acid groups, phosphonic ester groups, phosphine radicals, sulfoxide radicals, sulfonyl radicals, sulfide radicals, heteroaryl radicals, nitro groups, OCN, borane radicals, silyl groups, stannate radicals, imino groups, hydrazine radicals, hydrazone radicals, oxime radicals, nitroso groups, diazo groups, phosphine oxide groups, hydroxyl groups or SCN groups. Very particular preference is given to F, Cl, CN, aryloxy, alkoxy, sulfonyl and heteroaryl.

Both in the symmetrical carbene ligands (IIb) and in the unsymmetrical carbene ligands (IIa), the moiety

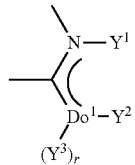

is preferably selected from the group consisting of

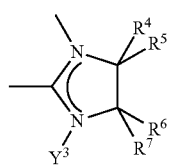

a

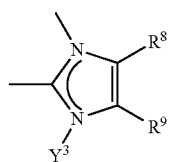

b

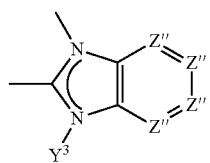

c

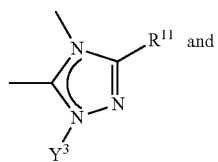

d

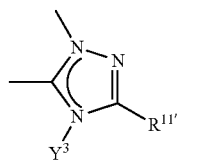

e in which the symbols are each defined as follows:

Z" are each independently $CR^{10}$ or N; preferably, from 0 to 3 of the Z" groups are N, more preferably from 0 to 2, most preferably 0 or 1, where the remaining Z" groups are $CR^{10}$;

$R^4$, $R^5$, $R^6$, $R^7$, $R^8$, $R^9$, $R^{11}$ and $R^{11'}$ are each hydrogen, alkyl, aryl, heteroaryl, alkynyl or alkenyl or a substituent with donor or acceptor action, preferably hydrogen, alkyl, heteroaryl or aryl;

$R^{10}$ is hydrogen, alkyl, aryl, heteroaryl, alkynyl or alkenyl, or in each case 2 $R^{10}$ radicals together form a fused ring which may optionally comprise at least one heteroatom, preferably N, or $R^{10}$ is a radical with donor or acceptor action, where at least one $R^{10}$ radical is preferably H, more preferably at least two $R^{10}$ radicals are each H, most preferably three or four $R^{10}$ radicals are each H;

in addition, R⁴ or R⁵ in the moiety a, R⁸ in the moiety b, one of the R¹⁰ radicals in the moiety c and R¹¹ in the moiety d may be bonded to R¹ via a bridge, where the bridge may be defined as follows:

alkylene, arylene, heteroarylene, alkynylene, alkenylene, NR¹⁸, PR¹⁹, BR²⁰, O, S, SO, SO₂, SiR³⁰R³¹, CO, CO—O, O—CO and (CR²¹R²²)ₓ, where one or more nonadjacent (CR²¹R²²) groups may be replaced by NR¹⁸, PR¹⁹, BR²⁰, O, S, SO, SO₂, SiR³⁰R³¹, CO, CO—O, O—CO, where x is from 2 to 10;

and

R¹⁸, R⁹, R²⁰, R²¹, R²², R³⁰, R³¹ are each H, alkyl, aryl, heteroaryl, alkenyl, alkynyl, where examples relating to bridges suitable with preference are shown above;

Y³ in at least one first carbene ligand (IIa) (unsymmetrical carbene ligand) is: hydrogen, an alkyl, alkynyl or alkenyl radical;

and

Y³ in at least one second carbene ligand (IIb) (symmetrical carbene ligand) is:

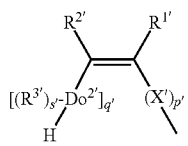

where Do²', q', s', R³', R¹', R²', X' and p' are each independently as defined for Do², q, s, R³, R¹, R², X and p.

Any further carbene ligands present in the inventive heteroleptic carbene complexes (when n in the carbene complexes of the formula I is >2) may be either symmetrical or unsymmetrical.

Both in the symmetrical carbene ligands (IIb) and in the unsymmetrical carbene ligands (IIa), the moiety

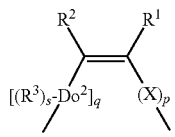

of the carbene ligand of the formula II preferably has the structure

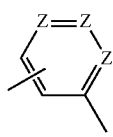

in which the symbols are each defined as follows:

Z are each independently CR¹² or N, where from 0 to 3 of the Z symbols may be N, preferably from 0 to 2, more preferably 0 or 1, and Z, in the case that 1 symbol Z is N, may be arranged in the o-, m- or p-position, preferably in the o- or p-position, to the bonding site of the moiety with the moiety

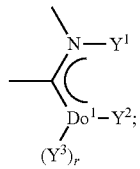

R¹² in the Z groups are each independently H, an alkyl, aryl, heteroaryl, alkynyl, alkenyl radical, or in each case 2 R¹² radicals together form a fused ring which may optionally comprise at least one heteroatom, preferably N, or R¹² is a radical with donor or acceptor action; preferably H or a radical with donor or acceptor action;

in addition, the group of the structure

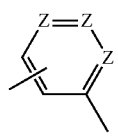

via the aromatic base structure or via one of the R¹² radicals, may be bonded to Y¹ via a bridge, where the bridge may be defined as follows:

alkylene, arylene, heteroarylene, alkynylene, alkenylene, NR¹⁸, PR¹⁹, BR²⁰, O, S, SO, SO₂, SiR³⁰R³¹, CO, CO—O, O—CO and (CR²¹R²²)ₓ, where one or more nonadjacent (CR²¹R²²) groups may be replaced by NR¹⁸, PR¹⁹, BR²⁰, O, S, SO, SO₂, SiR³⁰R³¹, CO, CO—O, O—CO, where x is from 2 to 10;

and

R¹⁸, R¹⁹, R²⁰, R²¹, R²², R³⁰, R³¹ are each H, alkyl, aryl, heteroaryl, alkenyl, alkynyl.

According to the invention, the Y³ radical in the unsymmetrical carbene ligands (IIa) is hydrogen, an alkyl, alkynyl or alkenyl radical, where, when Do¹ is C or Si and r is 2 in the carbene ligands of the general formula II, the two Y³ radicals are each as defined above. In a preferred embodiment, Do¹ is N and r 1. Preferred alkyl, alkynyl and alkenyl radicals are specified above. The Y³ radical in the unsymmetrical carbene ligands is more preferably an alkyl radical, most preferably methyl, ethyl, isopropyl, n-propyl, n-butyl, isobutyl or tert-butyl, especially preferably methyl or isopropyl.

According to the invention, the Y³ radical in the symmetrical carbene ligands (IIb) is:

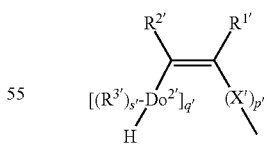

where Do²', q', s', R³', R¹', R²', X' and p' are each independently as defined for Do², q, s, R³, R¹, R², X and p—which have each already been defined above—and, when Do¹ is C or Si and r is 2, at least one of the two Y³ radicals is as defined above; the second Y³ radical may have the aforementioned definition or be as defined for Y³ with regard to the unsymmetrical carbene ligand. In a preferred embodiment, Do¹ is N and r is 1, i.e. the Y³ radical is as defined above.

In a preferred embodiment of the present invention, the group

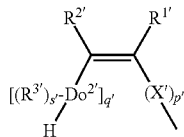

in the symmetrical carbene ligands is defined as follows:

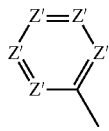

in which the symbols are each defined as follows:

Z' are each independently $CR^{12'}$ or N, where from 0 to 5 of the symbols Z' may each be N, preferably from 0 to 4, more preferably from 0 to 3, most preferably from 0 to 2, especially preferably 0 or 1, and Z', in the case that 1 symbol Z' is N, may be arranged in the o-, m- or p-position, preferably in the o- or p-position, to the bonding site of the moiety with the moiety

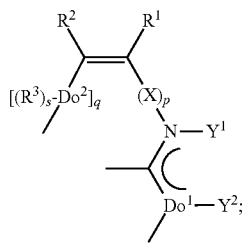

$R^{12'}$ in the Z' groups are each independently H, an alkyl, aryl, heteroaryl, alkynyl, alkenyl radical, or in each case 2 $R^{12'}$ radicals together form a fused ring which may optionally comprise at least one heteroatom, preferably N, or $R^{12'}$ is a radical with donor or acceptor action; preferably H or a radical with donor or acceptor action;

in addition, the group of the structure

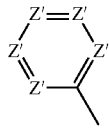

via the aromatic base structure or via one of the $R^{12'}$ radicals, may be bonded to $Y^1$ via a bridge, where the bridge may be defined as follows:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;
and
$R^{18}$, $R^{19}$, $R^{20}$, $R^{21}$, $R^{22}$, $R^{30}$, $R^{31}$
are each H, alkyl, aryl, heteroaryl, alkenyl, alkynyl.

If n is >2 in the heteroleptic carbene complexes of the general formula I, for example n=3 when $M^1$=Ir(III), the further $Y^3$ radical or radicals may either be as defined for the first (unsymmetrical) carbene ligand (IIa) or be as defined for the second (symmetrical) carbene ligand (IIb).

In addition, $Y^3$ and $Y^2$ in each of the n carbene ligands of the general formula II may be bonded to one another via a bridge, where the bridge may be defined as follows:
alkylene, arylene, heteroarylene, alkynylene, alkenylene, $NR^{25}$, $PR^{26}$, $BR^{27}$, O, S, SO, $SO_2$, $SiR^{32}R^{33}$, CO, CO—O, O—CO and $(CR^{28}R^{29})_y$, where one or more nonadjacent $(CR^{28}R^{29})$ groups may be replaced by $NR^{25}$, $PR^{26}$, $BR^{27}$, O, S, SO, $SO_2$, $SiR^{32}R^{33}$, CO, CO—O, O—CO, where
y is from 2 to 10;
and
$R^{25}$, $R^{26}$, $R^{27}$, $R^{28}$, $R^{29}$, $R^{32}$, $R^{33}$
are each H, alkyl, aryl, heteroaryl, alkenyl, alkynyl.

In a very particularly preferred embodiment, the present invention relates to heteroleptic carbene complexes of the formula I in which the at least one first (unsymmetrical) carbene ligand is selected from the group consisting of:

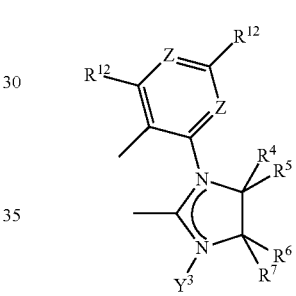

aa

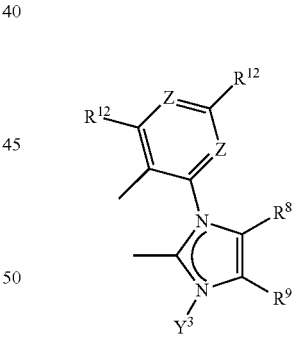

ab

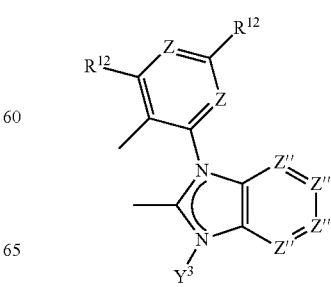

ac

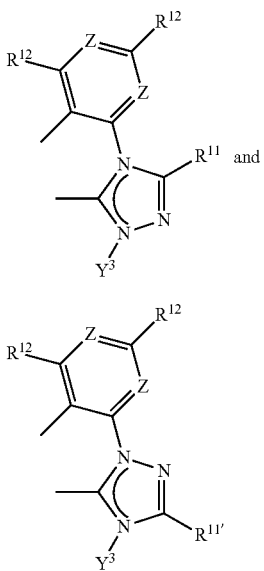

where the symbols are each defined as follows:

Z is the same or different and is $CR^1$ or N;

Z" is the same or different and is $CR^{10}$ or N;

$R^{12}$ are each independently H, an alkyl, aryl, heteroaryl, alkynyl or alkenyl radical, or in each case 2 $R^{12}$ radicals together form a fused ring which may optionally comprise at least one heteroatom, or $R^{12}$ is a radical with donor or acceptor action;

$R^4$, $R^5$, $R^6$, $R^7$, $R^1$, $R^9$, $R^{11}$ and $R^{11'}$ are each hydrogen, alkyl, aryl, heteroaryl, alkynyl or alkenyl, or a radical with donor or acceptor action;

$R^{10}$ in the Z" groups are each independently H, alkyl, aryl, heteroaryl, alkynyl or alkenyl, or in each case 2 $R^{10}$ radicals together form a fused ring which may optionally comprise at least one heteroatom, or $R^{10}$ is a radical with donor or acceptor action;

in addition, the group of the structure

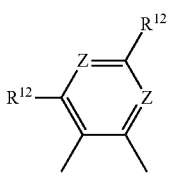

via the aromatic base structure or via one of the $R^{12}$ radicals, may be bonded via a bridge to $R^4$ or $R^5$ or the carbon atom to which $R^4$ and $R^5$ are bonded in the moiety aa, $R^8$ or the carbon atom to which $R^8$ is bonded in the moiety ab, one of the $R^{10}$ radicals or one of the carbon atoms to which $R^{10}$ is bonded in the moiety ac, and $R^{11}$ or the carbon atom to which $R^{11}$ is bonded in the moiety ad, where the bridge may be defined as follows:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}$, $R^{19}$, $R^{20}$, $R^{21}$, $R^{22}$, $R^{30}$, $R^{31}$ are each H, alkyl, aryl, heteroaryl, alkenyl, alkynyl;

where, in the cases in which the group of the structure

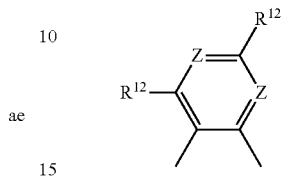

is bonded via a bridge to the carbon atom to which $R^4$ and $R^5$ are bonded (moiety aa), the carbon atom to which $R^8$ is bonded (moiety ab), one of the carbon atoms to which $R^{10}$ is bonded (moiety ac) or the carbon atom to which $R^{11}$ is bonded (moiety ad), the particular $R^4$ or $R^5$ radical, $R^8$, one of the $R^{10}$ radicals or $R^{11}$ is replaced by a bond to the bridge;

$Y^3$ is an alkyl, alkynyl or alkenyl radical.

In a further very particularly preferred embodiment, the present invention relates to heteroleptic carbene complexes of the formula I in which the at least one second (symmetrical) carbene ligand is selected from the group consisting of:

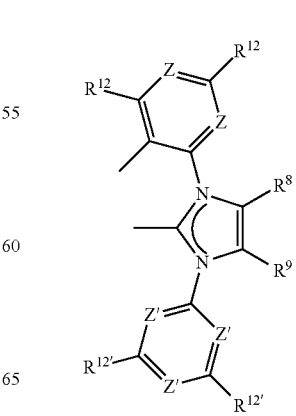

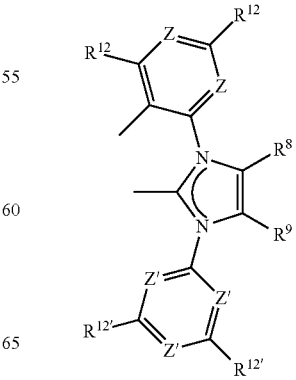

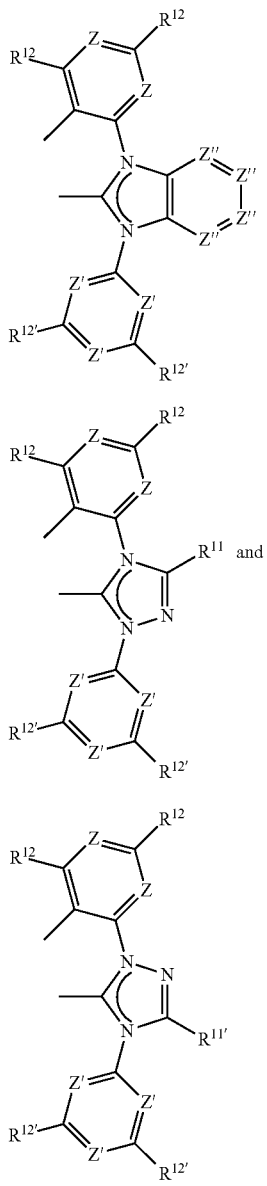

where the symbols are each defined as follows:

Z is the same or different and is $CR^{12}$ or N;

Z' is the same or different and is $CR^{12'}$ or N;

Z" is the same or different and is $CR^{10}$ or N;

$R^{12}$, $R^{12'}$ are the same or different and are each independently H, an alkyl, aryl, heteroaryl, alkynyl or alkenyl radical, or in each case 2 $R^{12}$ or $R^{12'}$ radicals together form a fused ring which may optionally comprise at least one heteroatom, or $R^{12}$ or $R^{12'}$ is a radical with donor or acceptor action;

$R^4$, $R^5$, $R^6$, $R^7$, $R^8$, $R^9$, $R^{11}$ and R''' are each hydrogen, alkyl, aryl, heteroaryl, alkynyl or alkenyl, or a radical with donor or acceptor action;

$R^{10}$ in the Z" groups are each independently H, alkyl, aryl, heteroaryl, alkynyl or alkenyl, or in each case 2 $R^{10}$ radicals together form a fused ring which may optionally comprise at least one heteroatom, or $R^{10}$ is a radical with donor or acceptor action;

in addition, the group of the structure

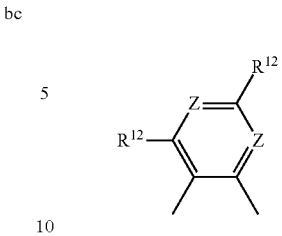

via the aromatic base structure or via one of the $R^{12}$ radicals, may be bonded via a bridge to $R^4$ or $R^5$ or the carbon atom to which $R^4$ and $R^5$ are bonded in the moiety ba, $R^8$ or the carbon atom to which $R^8$ is bonded in the moiety bb, one of the $R^{10}$ radicals or one of the carbon atoms to which $R^{10}$ is bonded in the moiety bc, and $R^{11}$ or the carbon atom to which $R^{11}$ is bonded in the moiety bd, where the bridge may be defined as follows:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}$, $R^{19}$, $R^{20}$, $R^{21}$, $R^{22}$, $R^{30}$, $R^{31}$ are each H, alkyl, aryl, heteroaryl, alkenyl, alkynyl;

where, in the cases in which the group of the structure

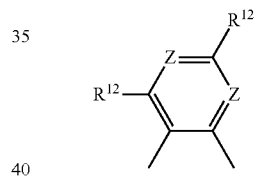

is bonded via a bridge to the carbon atom to which $R^4$ and $R^5$ are bonded (moiety ba), the carbon atom to which $R^8$ is bonded (moiety bb), one of the carbon atoms to which $R^{10}$ is bonded (moiety bc) or the carbon atom to which $R^{11}$ is bonded (moiety bd), the particular $R^4$ or $R^5$ radical, $R^8$, one of the $R^{10}$ radicals or $R^{11}$ is replaced by a bond to the bridge.

Very particular preference is given to heteroleptic carbene complexes of the formula I which comprise at least one first (unsymmetrical) carbene ligand of the aforementioned very particularly preferred embodiment and at least one second (symmetrical) carbene ligand of the aforementioned further very particularly preferred embodiment. When n in the inventive heteroleptic carbene complexes of the formula I is >2, the one further carbene ligand is, or the plurality of further carbene ligands are, in a further preferred embodiment, likewise either symmetrical or unsymmetrical carbene complexes of the aforementioned very particularly preferred embodiments.

The metal atom $M^1$ in the inventive heteroleptic carbene complexes of the general formula I is more preferably selected from the group consisting of Ir, Os, Rh and Pt, preference being given to Os(II), Rh(III), Ir(III) and Pt(II). Particular preference is given to Ir(III). Very particular preference is given to heteroleptic carbene complexes in which $M^1$ is Ir(III) and n is 3.

In a very particularly preferred embodiment, the inventive heteroleptic carbene complexes thus have the formulae (Ii) and (Iii):

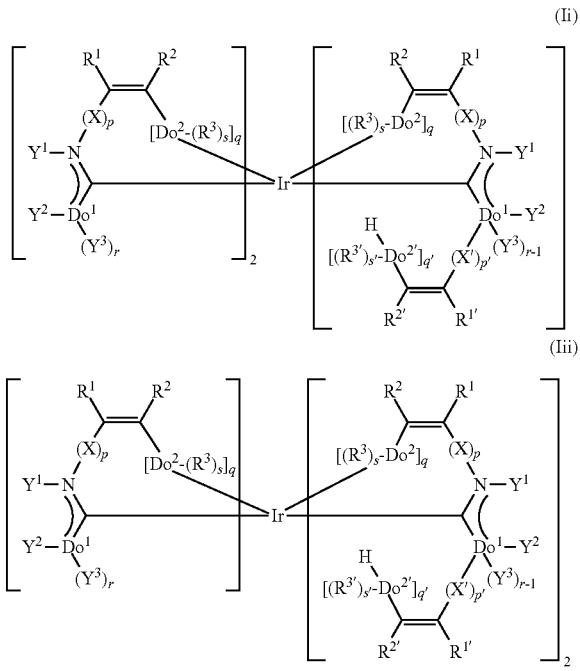

where the symbols in the carbene complexes of the general formulae (Ii) and (Iii) are each defined as follows:

$Do^1$ is a donor atom selected from the group consisting of C, P, N, O, S and Si, preferably P, N, O and S, where, in the carbene ligand

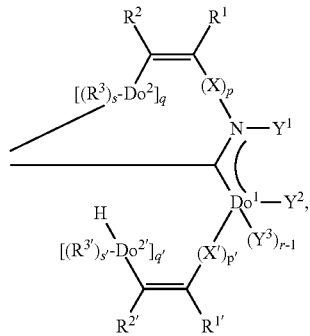

$Do^1$ is not O or S;

$Do^2$, $Do^{2'}$ are each independently a donor atom selected from the group consisting of C, N, P, O and S;

r is 2 when $Do^1$ is C or Si, is 1 when $Do^1$ is N or P, and is 0 when $Do^1$ is O or S;

s, s' are each 2 when $Do^2$ or $Do^{2'}$ is C, are each 1 when $Do^2$ or $Do^{2'}$ is N or P, and are each 0 when $Do^2$ or $Do^{2'}$ is O or S;

X, X' are each independently spacers selected from the group consisting of silylene, alkylene, arylene, heteroarylene, alkynylene, alkenylene, $NR^{13}$, $PR^{14}$, $BR^{15}$, O, S, SO, $SO_2$, CO, CO—O, O—CO and $(CR^{16}R^{17})_w$, where one or more nonadjacent $(CR^{16}R^{17})$ groups may be replaced by $NR^{13}$, $PR^{14}$, $BR^{15}$, O, S, SO, $SO_2$, CO, CO—O, O—CO;

w is from 2 to 10;

$R^{13}$, $R^{14}$, $R^{15}$, $R^{16}$, $R^{17}$
are each H, alkyl, aryl, heteroaryl, alkenyl, alkynyl;

p, p' are each independently 0 or 1;

q, q' are each independently 0 or 1;

$Y^1$, $Y^2$ are each independently hydrogen or a carbon group selected from the group consisting of alkyl, aryl, heteroaryl, alkynyl and alkenyl groups; or $Y^1$ and $Y^2$ together form a bridge between the donor atom $Do^1$ and the nitrogen atom N which has at least two atoms, of which at least one is a carbon atom, $R^1$, $R^2$, $R^{1'}$, $R^{2'}$ are each independently hydrogen, alkyl, aryl, heteroaryl, alkynyl or alkenyl radicals, or $R^1$ and $R^2$ or $R^{1'}$ and $R^{2'}$ together form a bridge having a total of from three to five atoms, of which 1 to 5 atoms may be heteroatoms and the remaining atoms are carbon atoms, so that the group

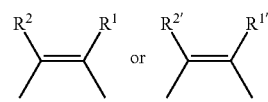

forms a five- to seven-membered ring which optionally—in addition to the double bond already present—may have one further double bond or—in the case of a six- or seven-membered ring—two further double bonds, and may optionally be substituted by alkyl or aryl groups and/or groups with donor or acceptor action, and may optionally comprise at least one heteroatom, and the five- to seven-membered ring may optionally be fused to one or more further rings, preferably six-membered aromatic rings;

in addition, $Y^1$ and $R^1$ or $Y^2$ and $R^{1'}$ may be bonded to one another via a bridge, where the bridge may be defined as follows:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}$, $R^{19}$, $R^{20}$, $R^{21}$, $R^{22}$, $R^{30}$, $R^{31}$
are each H, alkyl, aryl, heteroaryl, alkenyl, alkynyl;

$R^3$ is hydrogen, an alkyl, aryl, heteroaryl, alkynyl or alkenyl radical;

$Y^3$ is hydrogen, an alkyl, alkynyl or alkenyl radical;

in addition, $Y^3$ and $Y^2$ may be bonded to one another via a bridge, where the bridge may be defined as follows:

alkylene, arylene, heteroarylene, alkynylene, alkenylene, $NR^{25}$, $PR^{26}$, $BR^{27}$, O, S, SO, $SO_2$, $SiR^{32}R^{33}$, CO, CO—O, O—CO and $(CR^{28}R^{29})_y$, where one or more nonadjacent $(CR^{28}R^{29})$ groups may be replaced by $NR^{25}$, $PR^{26}$, $BR^{27}$, O, S, SO, $SO_2$, $SiR^{32}R^{33}$, CO, CO—O, O—CO, where y is from 2 to 10;

and $R^{25}$, $R^{26}$, $R^{27}$, $R^{28}$, $R^{29}$, $R^{32}$, $R^{33}$
are each H, alkyl, aryl, heteroaryl, alkenyl, alkynyl;

where the radicals, groups and indices $R^1$, $R^2$, $Y^1$, $Y^2$, $Do^1$, $Do^2$, X, $R^3$, p, q, r, s, $R^{1'}$, $R^{2'}$, $Do^{2'}$, $R^3$, p', q', s' in the different carbene ligands may each be the same or different.

A preferred embodiment of the invention thus relates to heteroleptic Ir(III)-carbene complexes of the formula (Ii)

which have two unsymmetrical carbene ligands and one symmetrical carbene ligand, and a further preferred embodiment of the invention to heteroleptic Ir(III)-carbene complexes of the formula (Iii) which have two symmetrical carbene ligands and one unsymmetrical carbene ligand. The two unsymmetrical carbene ligands in the carbene complexes of the formula (Ii) and the two symmetrical carbene ligands in the carbene complexes of the formula (Iii) may each be the same or different. The two unsymmetrical carbene ligands in the carbene complexes of the formula (Ii) and the two symmetrical carbene ligands in the carbene complexes of the formula (Iii) are preferably the same in each case. Preferred and very particularly preferred symmetrical and preferred and very particularly preferred unsymmetrical carbene ligands have been mentioned above.

Very particularly preferred ligand combinations of the unsymmetrical ligands aa to ae and symmetrical ligands ba to be to be used with very particular preference in the heteroleptic carbene complexes of the formulae Ii and Iii ($M^1$ is Ir(III) and n is 3) are listed in the table below:

| unsymmetrical carbene ligand | symmetrical carbene ligand | | | | |
|---|---|---|---|---|---|
| | ba | bb | bc | bd | be |
| aa | +[1)] | + | + | + | + |
| ab | + | + | + | + | + |
| ac | + | + | + | + | + |
| ad | + | + | + | + | + |
| ae | + | + | + | + | + |

[1)] "+" denotes possible combination of symmetrical and unsymmetrical carbene ligands In the carbene complexes of the formula II, the number of unsymmetrical ligands aa to ae is 2 and the number of symmetrical ligands ba to be is 1, and, in the carbene complexes of the formula Iii, the number of unsymmetrical ligands aa to ae is 1 and the number of symmetrical ligands ba to be is 2. Very particular preference is given in particular to the following ligand combinations: unsymmetrical carbene ligand: ab—symmetrical carbene ligand: bb; unsymmetrical carbene ligand: ab—symmetrical carbene ligand: bc; unsymmetrical carbene ligand: ac—symmetrical carbene ligand: bb; unsymmetrical carbene ligand: ac—symmetrical carbene ligand: bc.

Particular preference is given to heteroleptic carbene complexes of the formula II which have two unsymmetrical carbene ligands and one symmetrical carbene ligand of the formula II.

The inventive heteroleptic carbene complexes of the formula I can in principle be prepared analogously to processes known to those skilled in the art, taking into account the fact that the inventive heteroleptic carbene complexes of the formula I bear at least two different carbene ligands. Suitable processes for preparing carbene complexes are detailed, for example, in the review articles W. A. Hermann et al., Advances in Organometallic Chemistry, 2001 vol. 48, 1 to 69, W. A. Hermann et al., Angew. Chem. 1997, 109, 2256 to 2282 and G. Bertrand et al. Chem. Rev. 2000, 100, 39 to 91 and the literature cited therein, and also in WO 2005/113704, WO 2005/019373 and in European application EP 06 101 109.4 which had not been published at the priority date of the present application.

In one embodiment, the inventive heteroleptic carbene complexes of the formula I are prepared by deprotonating ligand precursors corresponding to the carbene ligands and subsequent reaction with suitable metal complexes comprising the desired metal.

Suitable ligand precursors of the symmetrical and unsymmetrical carbene ligands are known to those skilled in the art. They are preferably cationic precursors.

In a preferred embodiment, the present invention relates to a process for preparing the inventive heteroleptic carbene complexes of the general formula I, the preparation comprising the following step:
reaction of at least 2 ligand precursors of the general formula (III)

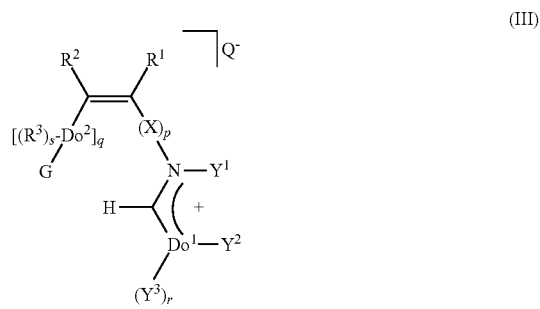

(III)

in which
$Q^-$ is a monoanionic counterion, preferably halide, pseudohalide, $BF_4^-$, $BPh_4^-$, $PF_6^-$, $AsF_6^-$ or $SbF_6^-$;
and
G is H when $Do^2=C$ or q=0, and
is H or is a free electron pair of the heteroatom when $Do^2=N$, S, O or P;
and
the further symbols in the ligand precursor of the general formula III are each defined
as follows:
$Do^1$ is a donor atom selected from the group consisting of C, P, N, O, S and Si, preferably P, N, O and S;
$Do^2$ is a donor atom selected from the group consisting of C, N, P, O and S;
r is 2 when $Do^1$ is C or Si, is 1 when $Do^1$ is N or P, and is 0 when $Do^1$ is O or S;
s is 2 when $Do^2$ is C, is 1 when $Do^2$ is N or P, and is 0 when $Do^2$ is O or S;
X is a spacer selected from the group consisting of silylene, alkylene, arylene, heteroarylene, alkynylene, alkenylene, $NR^{13}$, $PR^{14}$, $BR^{15}$, O, S, SO, $SO_2$, CO, CO—O, O—CO and $(CR^{16}R^{17})_w$, where one or more nonadjacent $(CR^{16}R^{17})$ groups may be replaced by $NR^{13}$, $PR^{14}$, $BR^5$, O, S, SO, $SO_2$, CO, CO—O, O—CO;
w is from 2 to 10;
$R^{13}$, $R^{14}$, $R^{15}$, $R^{16}$, $R^{17}$ are each
H, alkyl, aryl, heteroaryl, alkenyl, alkynyl;
p is 0 or 1;
q is 0 or 1;
$Y^1$, $Y^2$ are each independently hydrogen or a carbon group selected from the group consisting of alkyl, aryl, heteroaryl, alkynyl and alkenyl groups;
or
$Y^1$ and $Y^2$ together form a bridge between the donor atom $Do^1$ and the nitrogen atom N, said bridge having at least two atoms of which at least one is a carbon atom,
$R^{33}$, $R^2$ are each independently hydrogen, alkyl, aryl, heteroaryl, alkynyl or alkenyl radicals,
or
$R^1$ and $R^2$ together form a bridge having a total of from three to five atoms, of which from 1 to 5 atoms may be heteroatoms and the remaining atoms are carbon atoms, so that the group

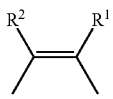

forms a five- to seven-membered ring which, if appropriate—in addition to the double bond already present—may have one further double bond or—in the case of a six- or seven-membered ring—two further double bonds, and may optionally be substituted by alkyl or aryl groups and/or groups with donor or acceptor action, and may optionally comprise at least one heteroatom, and the five- to seven-membered ring may optionally be fused to one or more further rings, preferably six-membered aromatic rings;

in addition, $Y^1$ and $R^1$ may be bonded to one another via a bridge, where the bridge may be defined as follows:

alkylene, arylene, heteroarylene, alkynylene, alkenylene, $NR^{18}$, $PR^{19}$, $BR^2$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}$, $R^{19}$, $R^{20}$, $R^{21}$, $R^{22}$, $R^{30}$, $R^{31}$ are each H, alkyl, aryl, heteroaryl, alkenyl, alkynyl;

$R^3$ is hydrogen, an alkyl, aryl, heteroaryl, alkynyl or alkenyl radical;

where the at least 2 ligand precursors of the general formula III have different definitions of $Y^3$, where $Y^3$ in at least one first ligand precursor (IIIa) is defined as follows:

hydrogen, an alkyl, alkynyl or alkenyl radical, where when $Do^1$ is C or Si and r is 2, the two $Y^3$ radicals are each as defined above;

and $Y^3$ in at least one second ligand precursor (IIIb) is defined as follows:

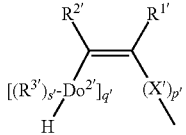

where $Do^{2'}$, $q'$, $s'$, $R^{3'}$, $R^{1'}$, $R^{2'}$, $X'$ and $p'$ are each independently as defined for $Do^2$, q, s, $R^3$, $R^1$, $R^2$, X and p, and when $Do^1$ is C or Si and r is 2, at least one of the two $Y^3$ radicals is as defined above; the second $Y^3$ radical may be as defined above or be as defined for $Y^3$ with regard to the first ligand precursor;

with a metal complex comprising at least one metal $M^{1'}$, where $M^{1'}$ is defined as follows:

$M^{1'}$ is a metal atom selected from the group consisting of Ir, Co, Rh, Ni, Pd, Pt, Fe, Ru, Os, Cr, Mo, W, Mn, Tc, Re, Cu and Au, preferably Ir, Os, Ru, Rh, Pd, Co and Pt, more preferably Ir, Pt, Rh and Os, in any oxidation state possible for the corresponding metal atom.

The metal $M^{1'}$ used is preferably Ir, more preferably Ir(1) or Ir(III).

Preferred definitions for $Do^1$, $Y^1$, $Y^2$, $Do^2$, q, s, $R^3$, $R^1$, $R^2$, X and p and $Do^{2'}$, $q'$, $s'$, $R^{3'}$, $R^{1'}$, $R^{2'}$, $X'$ and $p'$ in the ligand precursors of the general formula III are the definitions specified with regard to the carbene ligands of the general formula II. Preferred ligand precursors of the formula III correspond to the preferred symmetrical (IIb) and unsymmetrical (IIa) carbene ligands.

In the context of the present application, unsymmetrical ligand precursors (IIIa) (corresponding to unsymmetrical carbene ligands) are understood to mean those ligand precursors of the general formula III in which $Y^3$ is hydrogen, an alkyl, alkynyl or alkenyl radical, where, when $Do^1$ is C or Si and r is 2, the two $Y^3$ radicals are each as defined above.

Symmetrical ligand precursors (IIIb) (corresponding to symmetrical carbene ligands) are understood to mean those ligand precursors of the general formula III in which $Y^3$ is defined as follows:

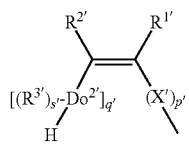

where $Do^{2'}$, $q'$, $s'$, $R^{3'}$, $R^{1'}$, $R^{2'}$, $X'$ and $p'$ are each independently as defined for $Do^2$, q, s, $R^3$, $R^1$, $R^2$, X and p, and when $Do^1$ is C or Si and r is 2, at least one of the two $Y^3$ radicals is as defined above; the second $Y^3$ radical may be as defined above or be as defined for $Y^3$ with regard to the first ligand precursor.

The preparation of the inventive heteroleptic carbene complexes is in principle possible by simultaneous reaction of symmetrical and unsymmetrical ligand precursors of the general formula III with a metal complex comprising at least one metal $M^{1'}$ ("one-pot process") or by sequential reaction. The sequential reaction can be effected either by reacting the metal complex with a symmetrical ligand precursor (IIIb) in a first step wherein, as an intermediate, a carbene complex which has at least one symmetrical carbene ligand either of the general formula IIb or as the non-cyclometalated form, and at least one further coordination means (where the further coordination means is present either by virtue of a free coordination site on the metal $M^{1'}$ or by virtue of the displacement of other ligands) for at least one further bidentate carbene ligand is formed, or by reacting the metal complex with an unsymmetrical ligand precursor (IIIa) in a first step wherein, as an intermediate, a carbene complex which has at least one unsymmetrical carbene ligand either of the general formula IIa or as the non-cyclometalated form, and at least one further coordination means (where the further coordination means is present either by virtue of a free coordination site on the metal $M^{1'}$ or by virtue of the displacement of other ligands) for at least one further bidentate carbene ligand is formed. In a second step which follows the first step, the particular carbene complex obtained in the first step is reacted with an unsymmetrical carbene ligand (when a symmetrical carbene ligand has been used in the first step) or with a symmetrical carbene ligand (when an unsymmetrical carbene ligand has been used in the first step).

In the particularly preferred case that the metal $M^1$ in the inventive heteroleptic carbene complexes of the formula I is Ir(III) with a coordination number of 6, a sequential reaction gives rise, for example, to the following particularly preferred possibilities:

(ia) Carbene Complex of the General Formula Ii (iaa) Reaction of a metal complex comprising at least one metal $M^{1'}$ in which the at least one metal $M^{1'}$ is Ir with at least double the stoichiometric amount, in relation to Ir, of an unsymmetrical ligand precursor (IIIa) to form a dicarbene complex which has two unsymmetrical carbene ligands and a further coordination site for a further bidentate carbene ligand, and (iab) subsequent reaction of the resulting dicarbene complex with an at least stoichiometric amount, in relation to Ir, of a symmetrical ligand precursor (IIIb) to obtain a heteroleptic Ir-carbene complex of the general formula II.

(ib) Carbene Complex of the General Formula Ii (iba) Reaction of a metal complex comprising at least one metal $M^{1'}$ in which the at least one metal $M^{1'}$ is Ir with an at least stoichiometric amount, in relation to Ir, of a symmetrical ligand precursor (IIIb) to form a monocarbene complex which has a symmetrical carbene ligand and two further coordination sites for two further bidentate carbene ligands, and (ibb) subsequent reaction of the resulting monocarbene complex with at least double the stoichiometric amount, in relation to Ir, of an unsymmetrical ligand precursor (IIIa) to obtain a heteroleptic Ir-carbene complex of the general formula Ii.

(iia) Carbene Complex of the General Formula Iii (iiaa) Reaction of a metal complex comprising at least one metal $M^{1'}$ in which the at least one metal $M^{1'}$ is Ir with at least double the stoichiometric amount, in relation to Ir, of a symmetrical ligand precursor (IIIb) to form a dicarbene complex which has two symmetrical carbene ligands and a further coordination site for a further bidentate carbene ligand, and (iiab) subsequent reaction of the resulting dicarbene complex with an at least stoichiometric amount, in relation to Ir, of an unsymmetrical ligand precursor (IIIa) to obtain a heteroleptic Ir-carbene complex of the general formula Iii.

(iib) Carbene Complex of the General Formula Iii (iiba) Reaction of a metal complex comprising at least one metal $M^{1'}$ in which the at least one metal $M^{1'}$ is Ir with an at least stoichiometric amount, in relation to Ir, of an unsymmetrical ligand precursor (IIIa) to form a monocarbene complex which has an unsymmetrical carbene ligand and two further coordination sites for two further bidentate carbene ligands, and (iibb) subsequent reaction of the resulting monocarbene complex with an at least double the stoichiometric amount, in relation to Ir, of a symmetrical ligand precursor (IIIb) to obtain a heteroleptic Ir-carbene complex of the general formula Iii.

In the intermediates formed in steps (iaa), (iba), (iiaa) and (iiba), the particular carbene ligands may be present either in cyclometalated form or in non-cyclometalated form.

The aforementioned mono- and dicarbene complexes can, if appropriate, be isolated or be reacted with the further carbene ligand "in situ", i.e. without workup.

The ligand precursors of the formula III are prepared by processes known to those skilled in the art. Suitable processes are mentioned, for example, in WO 2005/019373 and the literature cited therein, for example Organic Letters, 1999, 1, 953-956; Angewandte Chemie, 2000, 112, 1672-1674. Further suitable processes are mentioned, for example, in T. Weskamp et al., J. Organometal. Chem. 2000, 600, 12-22; G. Xu et al., Org. Lett. 2005, 7, 4605-4608; V. Lavallo et al., Angew. Chem. Int. Ed. 2005, 44, 5705-5709. Some of the suitable ligand precursors are commercially available.

The metal complex comprising at least one metal $M^{1'}$ is a metal complex comprising at least one metal selected from the group consisting of Ir, Co, Rh, Ni, Pd, Pt, Fe, Ru, Os, Cr, Mo, W, Mn, Tc, Re, Cu and Au, preferably Ir, Os, Ru, Rh, Pd, Co and Pt, more preferably Ir, Pt, Rh and Os, most preferably Ir, in any oxidation state possible for the corresponding metal atom, preferably Ir(I) or Ir(III). Suitable metal complexes are known to those skilled in the art. Examples of suitable metal complexes are $Pt(cod)Cl_2$, $Pt(cod)Me_2$, $Pt(acac)_2$, $Pt(PPh_3)_2Cl_2$, $PtCl_2$, $[Rh(cod)Cl]_2$, $Rh(acac)CO(PPh_3)$, $Rh(acac)(CO)_2$, $Rh(cod)_2BF_4$, $RhCl(PPh_3)_3$, $RhCl_3.n\ H_2O$, $Rh(acac)_3$, $[Os(CO)_3I_2]_2$, $[Os_3(CO)_{12}]$, $OsH_4(PPh_3)_3$, $Cp_2Os$, $Cp^*_2Os$, $H_2OsCl_6\ 6H_2O$, $OsC_{13}H_2O)$, and $[(\mu\text{-}Cl)Ir(\eta^4\text{-}1,5\text{-}cod)]_2$, $[(\mu\text{-}Cl)Ir(\eta^2\text{-}coe)_2]_2$, $Ir(acac)_3$, $IrCl_3.n\ H_2O$, $(tht)_3IrCl_3$, $Ir(\eta^3\text{-}allyl)_3$, $Ir(\eta^3\text{-}methallyl)_3$, in which cod is cyclooctadiene, coe is cyclooctene, acac is acetylacetonate and tht is tetrahydrothiophene. The metal complexes can be prepared by processes known to those skilled in the art or are commercially available.

In the preparation of iridium(III) complexes of the general formula I ($M^1$ in formula I is Ir), which are particularly preferred in the present application, the aforementioned iridium(I) or (III) complexes can be used, especially $[(\mu\text{-}Cl)Ir(\eta^4\text{-}1,5\text{-}cod)]_2$, $[(\mu\text{-}Cl)Ir(\eta^2\text{-}coe)_2]_2$, $Ir(acac)_3$, $IrCl_3\ n\ H_2O$, $(tht)_3IrCl_3$, $Ir(\eta^3\text{-}allyl)_3$, $Ir(\eta^3\text{-}methallyl)_3$, in which cod is cyclooctadiene, coe is cyclooctene, acac is acetylacetonate and tht is tetrahydrothiophene.

After the reaction, the inventive heteroleptic carbene complex is worked up and, if appropriate, purified by processes known to those skilled in the art. Typically, the workup and purification are effected by extraction, column chromatography and/or recrystallization by processes known to those skilled in the art.

A process for preparing the inventive heteroleptic carbene complexes of the general formula I is detailed below by way of example using the example of the aforementioned reaction (ia) for the preparation of heteroleptic carbene complexes of the general formula Ii:

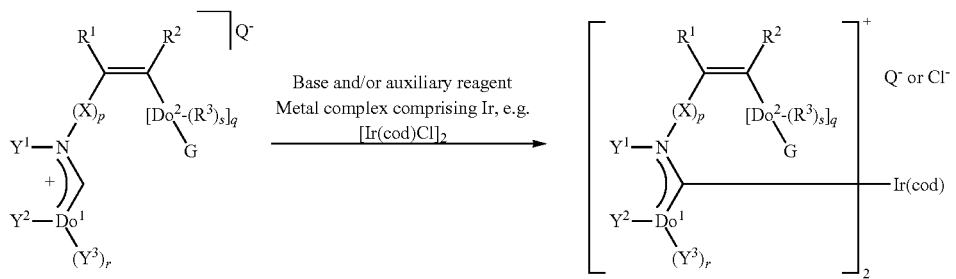
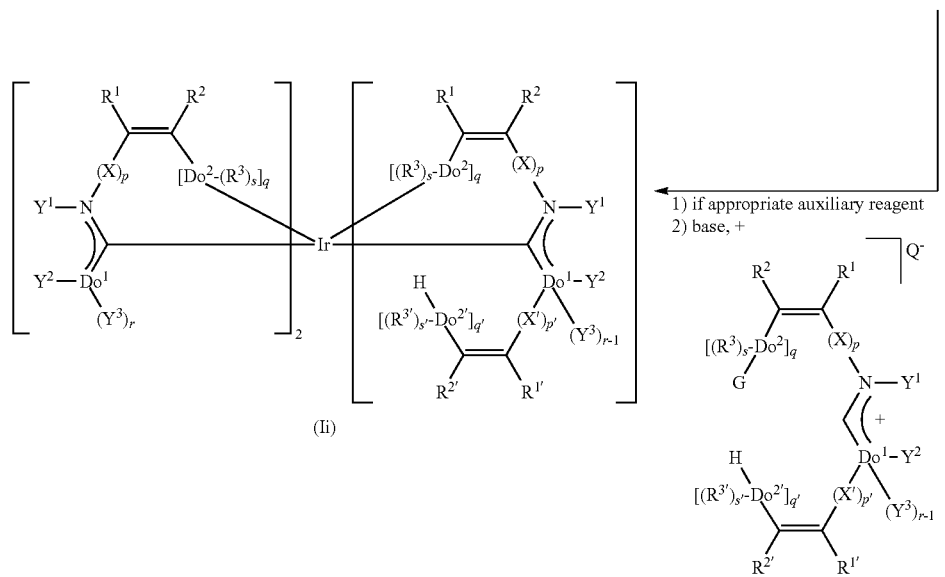
A further synthesis route (iia) to the preparation of the inventive heteroleptic carbene complexes is shown below by way of example:
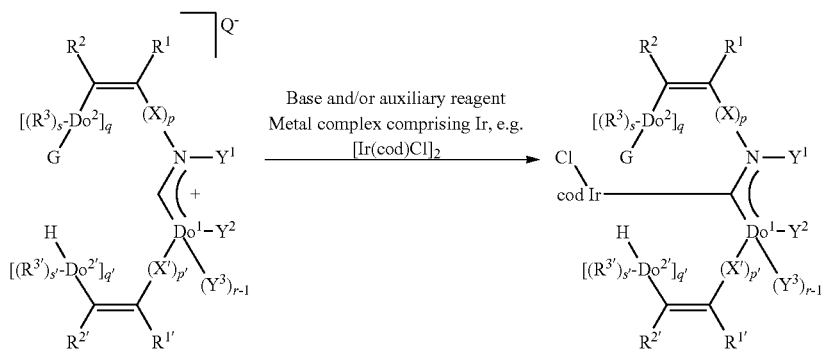

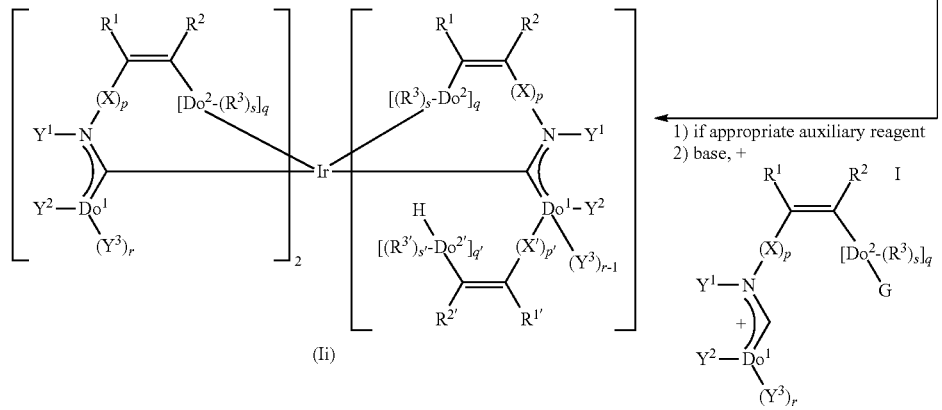

(Ii)

In addition, the inventive heteroleptic carbene complexes can be prepared, for example, analogously to WO 2005/113704, the following intermediate being passed through:

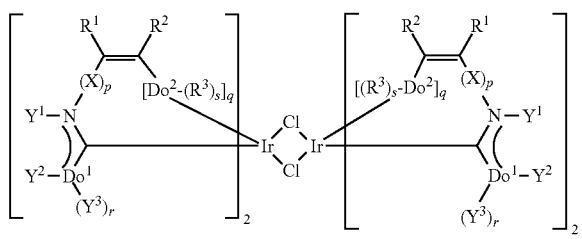

The symbols and radicals in the general formulae shown above have each already been defined above.

The inventive heteroleptic carbene complexes are outstandingly suitable as emitter substances, since they have an emission (electroluminescence) in the visible region of the electromagnetic spectrum. With the aid of the inventive heteroleptic carbene complexes as emitter substances, it is possible to provide compounds which exhibit electroluminescence in the red, green and in the blue region of the electromagnetic spectrum with very good efficiency. At the same time, the quantum yield is high and the stability of the inventive heteroleptic carbene complexes in the device is high.

In addition, the inventive heteroleptic carbene complexes are suitable as electron, exciton or hole blockers, or hole conductors, electron conductors, hole injection layer or matrix material in OLEDs, depending on the ligands used and the central metal used.

Organic light-emitting diodes (OLEDs) are in principle composed of several layers:
1. Anode (1)
2. Hole-transporting layer (2)
3. Light-emitting layer (3)
4. Electron-transporting layer (4)
5. Cathode (5)

However, it is also possible that the OLED does not have all of the layers mentioned; for example an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5), or the layers (1), (3), (4) and (5), are likewise suitable.

The heteroleptic carbene complexes according to the present application may be used in various layers of an OLED. The present invention therefore further provides for the use of the inventive heteroleptic carbene complexes in organic light-emitting diodes (OLEDs), and also an OLED comprising at least one inventive heteroleptic carbene complex.

The inventive heteroleptic carbene complexes are used preferably in the light-emitting layer, more preferably as emitter molecules. The present invention therefore further provides a light-emitting layer comprising at least one heteroleptic carbene complex, preferably as an emitter molecule. Preferred heteroleptic carbene complexes have been specified above.

The inventive heteroleptic carbene complexes may be present in bulk—without further additives—in the light-emitting layer or another layer of the OLED, preferably in the light-emitting layer. However, it is likewise possible and preferred that, in addition to the inventive heteroleptic carbene complexes, further compounds are present in the layers comprising at least one inventive heteroleptic carbene complex, preferably in the light-emitting layer. For example, a fluorescent dye may be present in the light-emitting layer in order to alter the emission color of the heteroleptic carbene complex used as an emitter molecule. In addition— in a preferred embodiment—a diluent material may be used. This diluent material may be a polymer, for example poly (N-vinylcarbazole) or polysilane. However, the diluent material may likewise be a small molecule, for example 4,4'-N,N'-dicarbazolebiphenyl (CDP=CBP) or tertiary aromatic amines.

The individual aforementioned layers of the OLED may in turn be composed of 2 or more layers. For example, the hole-transporting layer may be composed of one layer into which holes are injected from the electrode and one layer which transports the holes from the hole injection layer away into the light-emitting layer. The electron-transporting layer may likewise consist of a plurality of layers, for example one layer in which electrons are injected by the electrode and one layer which receives electrons from the electron injection layer and transports them into the light-emitting layer. These specified layers are each selected according to factors such as energy level, thermal resistance and charge carrier mobility, and also energy differential of the layers mentioned with the organic layers or the metal electrodes. Those skilled in the art are capable of selecting the structure of the OLEDs in such a way that it is adapted optimally to the heteroleptic carbene complexes used in accordance with the invention, preferably as emitter substances.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer should be aligned to the work function of the cathode.

The present application further provides an OLED comprising at least one inventive light-emitting layer. The further layers in the OLED may be composed of any material which is typically used in such layers and is known to those skilled in the art.

The anode (1) is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole-transporting materials for the layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole-transporting material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde-diphenylhydrazone (DE H), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4''-tris(N,N-diphenylamino)triphenylamine (TDTA) and porphyrin compounds, and also phthalocyanines such as copper phthalocyanines. Customarily used hole-transporting polymers are selected from the group consisting of polyvinylcarbazoles, (phenylmethyl)polysilanes, PEDOT (poly(3,4-ethylenedioxythiophene)), preferably PEDOT doped with PSS (polystyrenesulfonate), and polyanilines. It is likewise possible to obtain hole-transporting polymers by doping hole-transporting molecules into polymers such as polystyrene and polycarbonate. Suitable hole-transporting molecules are the molecules already mentioned above.

Suitable electron-transporting materials for the layer (4) of the inventive OLEDs comprise metals chelated with oxinoid compounds, such as tris(8-hydroxyquinolinolato) aluminum ($Alq_3$), compounds based on phenanthroline such as 2,9-dimethyl-4,7-diphenyl-1,10-phenanthroline (DDPA=BCP) or 4,7-diphenyl-1,10-phenanthroline (DPA) and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (4) may serve both to ease the electron transport and as a buffer layer or as a barrier layer in order to prevent quenching of the exciton at the interfaces of the layers of the OLED. The layer (4) preferably improves the mobility of the electrons and reduces quenching of the exciton.

Of the materials specified above as hole-transporting materials and electron-transporting materials, some can fulfill a plurality of functions. For example, some of the electron-conducting materials are simultaneously hole-blocking materials when they have a low-lying HOMO.

The charge transport layers may also be electronically doped in order to improve the transport properties of the materials used, in order firstly to make the layer thicknesses more generous (avoidance of pinholes/short circuits) and secondly to minimize the operating voltage of the device. For example, the hole-transporting materials may be doped with electron acceptors; for example, phthalocyanines or arylamines such as TPD or TDTA may be doped with tetrafluorotetracyanoquinodimethane (F4-TCNQ). The electron-transporting materials may, for example, be doped with alkali metals, for example $Alq_3$ with lithium. Electronic doping is known to those skilled in the art and is disclosed, for example, in W. Gao, A. Kahn, J. Appl. Phys., Vol. 94, No. 1, Jul. 1, 2003 (p-doped organic layers); A. G. Werner, F. Li, K. Harada, M. Pfeiffer, T. Fritz, K. Leo, Appl. Phys. Lett., Vol. 82, No. 25, Jun. 23, 2003 and Pfeiffer et al., Organic Electronics 2003, 4, 89-103.

The cathode (5) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. In addition, lithium-comprising organometallic compounds or LiF may be applied between the organic layer and the cathode in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:

a hole injection layer between the anode (1) and the hole-transporting layer (2);

a blocking layer for electrons and/or excitons between the hole-transporting layer (2) and the light-emitting layer (3);

a blocking layer for holes and/or excitons between the light-emitting layer (3) and the electron-transporting layer (4);

an electron injection layer between the electron-transporting layer (4) and the cathode (5).

As already mentioned above, it is, however, also possible that the OLED does not have all of the layers (1) to (5) mentioned; for example, an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5) or the layers (1), (3), (4) and (5) are likewise suitable.

Those skilled in the art know how suitable materials have to be selected (for example on the basis of electrochemical investigations). Suitable materials for the individual layers and suitable OLED structures are known to those skilled in the art and disclosed, for example, in WO2005/113704.

Furthermore, each of the specified layers of the inventive OLED may be composed of two or more layers. In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass or polymer films. For the vapor deposition, customary techniques may be used, such as thermal evaporation, chemical vapor deposition and others. In an alternative process, the organic layers may be coated from solutions or dispersions in suitable solvents, in which case coating techniques known to those skilled in the art are employed. Compositions which, in addition to the at least one inventive heteroleptic carbene complex, have a polymeric material in one of the layers of the OLED, preferably in the light-emitting layer, are generally applied as a layer by means of solution-mediated processes.

In general, the different layers have the following thicknesses: anode (1) from 500 to 5000 Å, preferably from 1000 to 2000 Å; hole-transporting layer (2) from 50 to 1000 Å, preferably from 200 to 800 Å; light-emitting layer (3) from 10 to 1000 Å, preferably from 100 to 800 Å; electron-transporting layer (4) from 50 to 1000 Å, preferably from 200 to 800 Å; cathode (5) from 200 to 10 000 Å, preferably from 300 to 5000 Å. The position of the recombination zone of holes and electrons in the inventive OLED and thus the emission spectrum of the OLED may be influenced by the relative thickness of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

Use of the inventive heteroleptic carbene complexes in at least one layer of the inventive OLED, preferably as an emitter molecule in the light-emitting layer of the inventive OLEDs, allows OLEDs with high efficiency to be obtained. The efficiency of the inventive OLEDs may additionally be improved by optimizing the other layers. For example, highly efficient cathodes such as Ca, Ba or LiF may be used. Shaped substrates and novel hole-transporting materials which bring about a reduction in the operating voltage or an increase in the quantum efficiency are likewise usable in the inventive OLEDs. Furthermore, additional layers may be present in the OLEDs in order to adjust the energy level of the different layers and to ease electroluminescence.

The inventive OLEDs may be used in all devices in which electroluminescence is useful. Suitable devices are preferably selected from stationary and mobile visual display units. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, vehicles and destination displays on buses and trains.

In addition, the inventive heteroleptic carbene complexes may be used in OLEDs with inverse structure. The inventive heteroleptic carbene complexes are preferably used in these inverse OLEDs again in the light-emitting layer. The structure of inverse OLEDs and the materials customarily used therein are known to those skilled in the art.

The above-described inventive heteroleptic carbene complexes may, in addition to the use in OLEDs, be used as colorants which emit in the visible region of the electromagnetic spectrum on irradiation by light (photoluminescence).

The present application therefore further provides for the use of the above-described inventive heteroleptic carbene complexes for the bulk coloration of polymeric materials.

Suitable polymeric materials are polyvinyl chloride, cellulose acetate, polycarbonates, polyamides, polyurethanes, polyimides, polybenzimidazoles, melamine resins, silicones, polyesters, polyethers, polystyrene, polymethyl methacrylate, polyethylene, polypropylene, polyvinyl acetate, polyacrylonitrile, polybutadiene, polychlorobutadiene, polyisoprene and the copolymers of the monomers listed.

In addition, the above-described inventive heteroleptic carbene complexes may be used in the following applications:

Use of the inventive heteroleptic carbene complexes as or in vat dye(s), for example for coloring natural materials; examples are paper, wood, straw, leather, pelts or natural fiber materials such as cotton, wool, silk, jute, sisal, hemp, flax or animal hairs (for example horsehair) and their conversion products, for example viscose fibers, nitrate silk or copper rayon.

Use of the inventive heteroleptic carbene complexes as colorants, for example for coloring paints, varnishes and other surface coating compositions, paper inks, printing inks, other inks and other colors for drawing and writing purposes.

Use of the inventive heteroleptic carbene complexes as pigmentary dyes, for example for coloring paints, varnishes and other surface coating compositions, paper inks, printing inks, other inks and other colors for drawing and writing purposes.

Use of the inventive heteroleptic carbene complexes as pigments in electrophotography: for example for dry copying systems (Xerox process) and laser printers.

Use of the inventive heteroleptic carbene complexes for security marking purposes, for which high chemical and photochemical stability and, if appropriate, also the luminescence of the substances is of significance. This is preferably for checks, check cards, banknotes, coupons, documents, identification papers and the like, in which a particular, unmistakable color impression is to be achieved.

Use of the inventive heteroleptic carbene complexes as an additive to other colors in which a particular shade is to be achieved; preference is given to particularly brilliant colors.

Use of the inventive heteroleptic carbene complexes for marking articles for machine recognition of these articles using the luminescence, preferably machine recognition of articles for sorting, including, for example, for the recycling of plastics.

Use of the inventive heteroleptic carbene complexes as luminescent dyes for machine-readable markings; preference is given to alphanumeric markings or barcodes.

Use of the inventive heteroleptic carbene complexes for adjusting the frequency of light, for example to convert short-wavelength light into longer-wavelength, visible light.

Use of the inventive heteroleptic carbene complexes in display elements for any kind of display, information and marking purposes, for example in passive display elements, information signs and traffic signs, such as traffic lights.

Use of the inventive heteroleptic carbene complexes in inkjet printers, preferably in homogeneous solution as luminescent ink.

Use of the inventive heteroleptic carbene complexes as a starting material for superconductive organic materials.

Use of the inventive heteroleptic carbene complexes for solid-state luminescent markings.

Use of the inventive heteroleptic carbene complexes for decorative purposes.

Use of the inventive heteroleptic carbene complexes for tracer purposes, for example in biochemistry, medicine, engineering and natural sciences. In this use, the dyes can be bonded covalently to substrates or via secondary valences such as hydrogen bonds or hydrophobic interactions (adsorption).

Use of the inventive heteroleptic carbene complexes as luminescent dyes in high-sensitivity detection methods (cf. C. Aubert, J. Füjnfschilling, I. Zschocke-Gränacher and H. Langhals, Z. Analyt. Chem. 320 (1985) 361).

Use of the inventive heteroleptic carbene complexes as luminescent dyes in scintillation devices.

Use of the inventive heteroleptic carbene complexes as dyes or luminescent dyes in optical light-collection systems.

Use of the inventive heteroleptic carbene complexes as dyes or luminescent dyes in luminescent solar collectors (cf. Langhals, Nachr. Chem. Tech. Lab. 28 (1980) 716).

Use of the inventive heteroleptic carbene complexes as dyes or luminescent dyes in luminescence-activated displays (cf. W. Greubel and G. Baur, Elektronik 26 (1977) 6).

Use of the inventive heteroleptic carbene complexes as dyes or luminescent dyes in cold light sources for light-induced polymerization for the production of plastics.

Use of the inventive heteroleptic carbene complexes as dyes or luminescent dyes for materials testing, for example in the production of semiconductor circuits.

Use of the inventive heteroleptic carbene complexes as dyes or luminescent dyes for the investigation of microstructures of integrated semiconductor components.

Use of the inventive heteroleptic carbene complexes as dyes or luminescent dyes in photoconductors.

Use of the inventive heteroleptic carbene complexes as dyes or luminescent dyes in photographic processes.

Use of the inventive heteroleptic carbene complexes as dyes or luminescent dyes in display, illumination or image conversion systems, in which excitation occurs by means of electrons, ions or UV radiation, for example in luminescent displays, Braun tubes or in fluorescent tubes.

Use of the inventive heteroleptic carbene complexes as dyes or luminescent dyes as part of an integrated semiconductor circuit, the dyes being used as such or in conjunction with other semiconductors, for example in the form of epitaxy.

Use of the inventive heteroleptic carbene complexes as dyes or luminescent dyes in chemiluminescent systems, for example in chemiluminescent illumination rods, in luminescent immunoassays or other luminescent detection methods.

Use of the inventive heteroleptic carbene complexes as dyes or luminescent dyes as signal colors, preferably for the optical emphasis of inscriptions and drawings or other graphical products, for individualizing signs and other articles in which a particular optical color impression is to be achieved.

Use of the inventive heteroleptic carbene complexes as dyes or luminescent dyes in dye lasers, preferably as luminescent dyes for generating laser beams.

Use of the inventive heteroleptic carbene complexes as active substances for nonlinear optics, for example for frequency doubling and frequency tripling of laser light.

Use of the inventive heteroleptic carbene complexes as rheology improvers.

Use of the inventive heteroleptic carbene complexes as dyes in photovoltaic applications for the conversion of electromagnetic radiation to electrical energy.

The examples which follow provide additional illustration of the invention.

EXAMPLES a) Synthesis of Complex K I

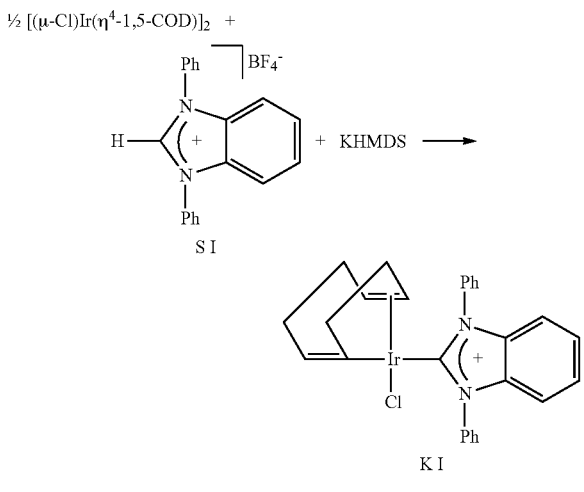

In a 1 l three-neck flask, 16.11 g (45 mmol) of benzimidazolium salt S I were suspended in 250 ml of toluene and cooled to −8° C. 90 ml of bis(trimethylsilyl)potassium amide (KHMDS, 0.5M in toluene, 45 mmol) are then added within 30 min. The mixture is stirred at room temperature for 1 hour and then added dropwise at −78° C. to a solution of 15.12 g (22.5 mmol) of [(μ-Cl)Ir(η$^4$-1,5-COD)]$_2$ in 400 ml of toluene within 30 min. The reaction mixture is stirred at room temperature for 1.5 h and then heated at reflux for 18 h. After cooling, the precipitate is filtered off and washed with toluene. The combined toluene phases are concentrated to dryness and purified by column chromatography. 13.4 g (49%) of yellow powder are obtained.

$^1$H NMR (CD$_2$Cl$_2$, 500 MHz): δ=7.96 (m, 4H), 7.51 (m, 6H), 7.25 (m, 2H), 7.18 (m, 2H) (je CH$_{Ph}$), 4.31 (m, 2H, CH$_{cod}$), 2.43 (m, 2H, CH$_{cod}$), 1.61 (m, 2H), 1.34 (m, 4H), 1.17 (m, 2H) (je CH$_{2,cod}$).

$^{13}$C NMR (CD$_2$Cl$_2$, 125 MHz): δ=191.5 (NCN), 137.0, 135.0 (C$_q$), 128.1, 127.8, 127.1, 122.5, 110.0 (CH$_{Ph}$), 84.5, 51.4 (je CH$_{cod}$), 32.1, 28.1 (je CH$_{2,cod}$).

b) Synthesis of Complex K II

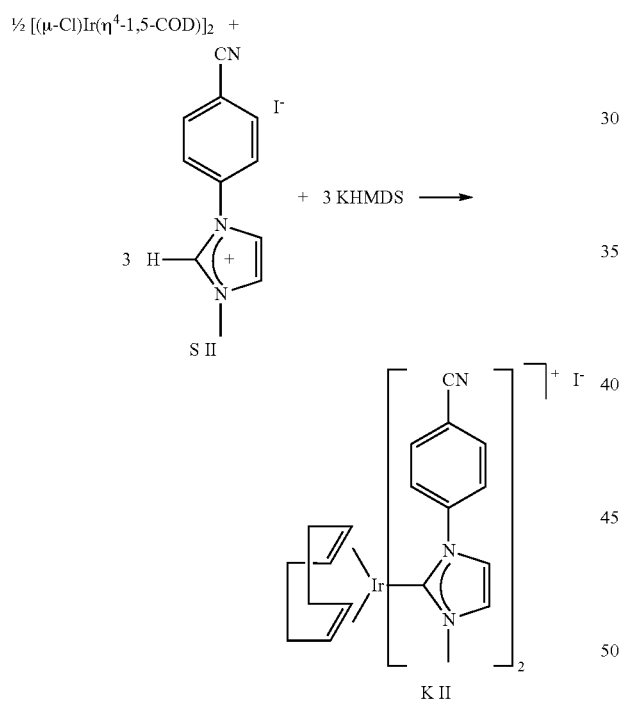

13.74 g (44.16 mmol) of imidazolium iodide S II are suspended in 200 ml of THF and admixed at −8° C. with 88.32 ml of bis(trimethylsilyl)potassium amide (0.5M in toluene, 44.16 mmol) within 30 min. The suspension is stirred at room temperature for 1 hour and then added dropwise at −78° C. to a solution of 4.94 g (7.36 mmol) of [(μ-Cl)Ir(η$^4$-1,5-COD)]$_2$ in 360 ml of THF within 30 min. The mixture is stirred at room temperature for 1.5 h and under reflux for 17 h. After cooling, the precipitate is filtered off, washed with THF, H$_2$O and methanol, and dried. 4.02 g (34%) of orange powder are obtained.

$^1$H NMR (DMSO, 500 MHz): δ=8.09 (d, $^3$J$_{H,H}$=7.8 Hz, 4H, CH$_{ph}$), 7.53 (d, $^3$J$_{H,H}$=7.8 Hz, 4H, CH$_{ph}$), 7.46 (s, 2H, NCHCHN), 7.34 (s, 2H, NCHCHN), 4.64 (m, 2H, CH$_{cod}$), 3.58 (m, 2H, CH$_{cod}$), 3.06 (s, 6H, NCH$_3$), 2.33-2.01 (m, 4H, CH$_{2,cod}$), 1.76-1.1.59 (m, 4H, CH$_{2,cod}$).

c) Synthesis of Complex K III (Route 1)

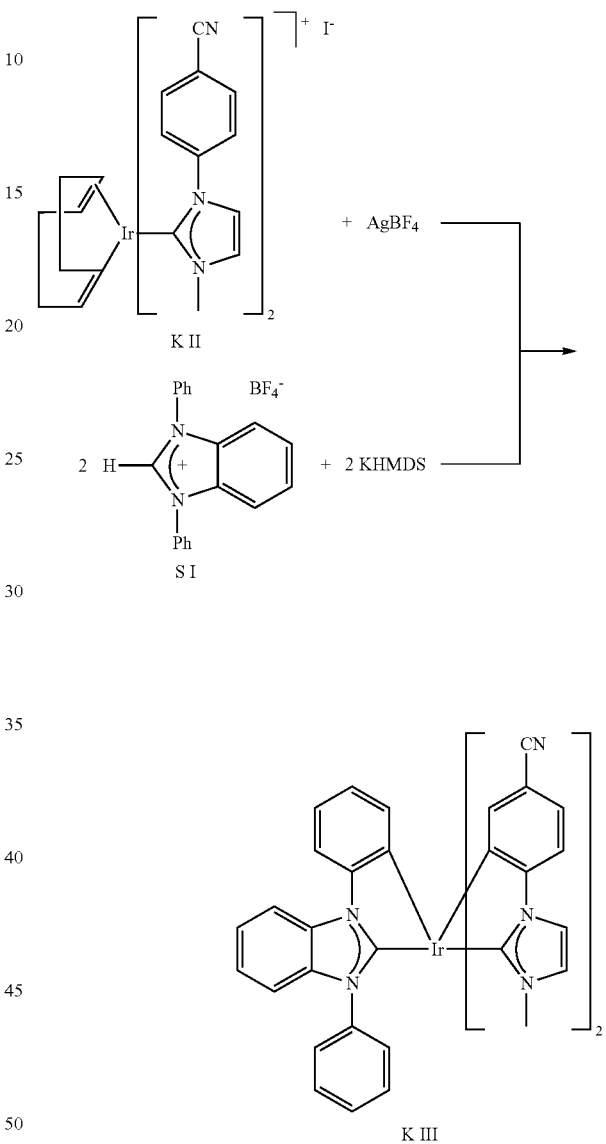

1.24 g (3.46 mmol) of benzimidazolium salt S I are suspended in 90 ml of dioxane. 6.9 ml of bis(trimethylsilyl) potassium amide (KHMDS, 0.5M in toluene, 3.45 mmol) are then added within 10 min. The mixture is stirred at room temperature for a half hour and then added dropwise to a mixture of 1.37 g (1.73 mmol) of K II and 0.34 g (1.73 mmol) of silver tetrafluoroborate in 90 ml of dioxane within 20 min. The reaction mixture is stirred at room temperature for 1 hour and then heated at reflux for 21 h. After cooling, the precipitate is filtered off and washed with dioxane. The filtrate is freed from the solvent and with extracted methylene chloride. 0.38 g (27%) of yellow powder is obtained from the extract after column chromatography purification.

d) Synthesis of Complex K III (Route 2)

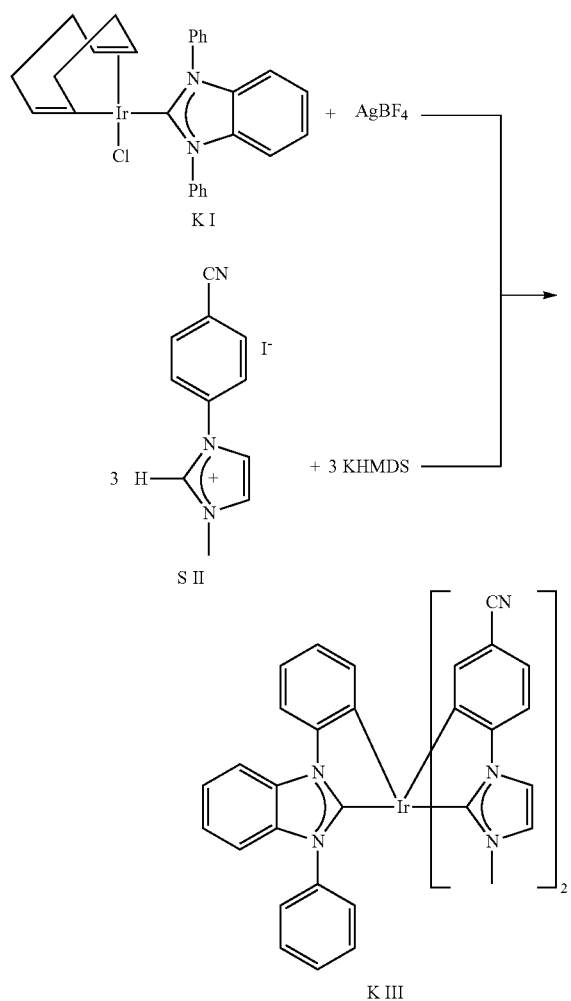

2.31 g (7.38 mmol) of imidazolium salt S II are suspended in 135 ml of dioxane. 14.8 ml of bis(trimethylsilyl)potassium amide (KHMDS, 0.5M in toluene, 7.40 mmol) are then added within 10 min. The mixture is stirred at room temperature for 1 hour and then added dropwise to a mixture of 1.5 g (2.46 mmol) of K I and 0.48 g (2.46 mmol) of silver tetrafluoroborate in 90 ml of dioxane within 20 min. The reaction mixture is stirred at room temperature for 1 hour and then heated at reflux for 21 h. After cooling, the precipitate is filtered off and washed with dioxane. The filtrate is freed from the solvent and with extracted methylene chloride. 0.70 g (34%) of slightly yellowish powder is obtained from the extract after column chromatography purification.

$^1$H NMR (CD$_2$Cl$_2$, 500 MHz): δ=2.44 (s, 3H), 3.21 (s, 3H), 6.21-6.23 (m, 1H), 6.26 (d, J=2.1 Hz, 1H), 6.51 (dd, J=7.3 Hz, J=1.5 Hz, 1H), 6.59-6.60 (m, 1H), 6.72 (dt, J=7.3 Hz, J=1.1 Hz, 1H), 6.77 (d, J=2.3 Hz, 1H), 6.81-6.82 (m, 1H), 6.85-6.87 (m, 1H), 7.06-7.19 (m, 4H), 7.21-7.26 (m, 3H), 7.28-7.33 (m, 2H), 7.35-7.39 (m, 2H), 7.43-7.49 (m, 2H), 7.98 (d, J=7.9 Hz, 1H), 8.25 (d, J=8.2 Hz, 1H).

$^{13}$C NMR (CD$_2$Cl$_2$, 126 MHz): δ=36.5 (CH$_3$), 37.5 (CH$_3$), 108.02 (C$_q$, CN), 108.04 (C$_q$, CN), 110.5 (CH), 110.9 (CH), 111.2 (CH), 111.7 (CH), 113.0 (CH), 114.6 (CH), 115.1 (CH), 121.0 (C$_q$), 121.1 (C$_q$), 121.66 (CH), 121.73 (CH), 121.8 (CH), 122.7 (CH), 123.8 (CH), 125.3 (CH), 126.3 (CH), 126.5 (CH), 126.7 (CH), 128.6 (CH), 128.8 (CH), 129.1 (CH), 130.0 (CH), 132.7 (C$_q$), 137.4 (CH), 138.2 (C$_q$), 138.4 (C$_q$), 140.2 (CH), 141.3 (CH), 147.2 (C$_q$), 149.1 (C$_q$), 149.7 (C$_q$), 150.7 (C$_q$), 151.17 (C$_q$), 151.23 (C$_q$), 176.6 (C$_q$, NCN), 177.5 (C$_q$, NCN), 187.1 (C$_q$, NCN).

e) Optical Spectroscopy

Photoluminescence (Polymethyl Methacrylate (PMMA) Films Doped with 2% by Weight of the Particular Carbene Complex)

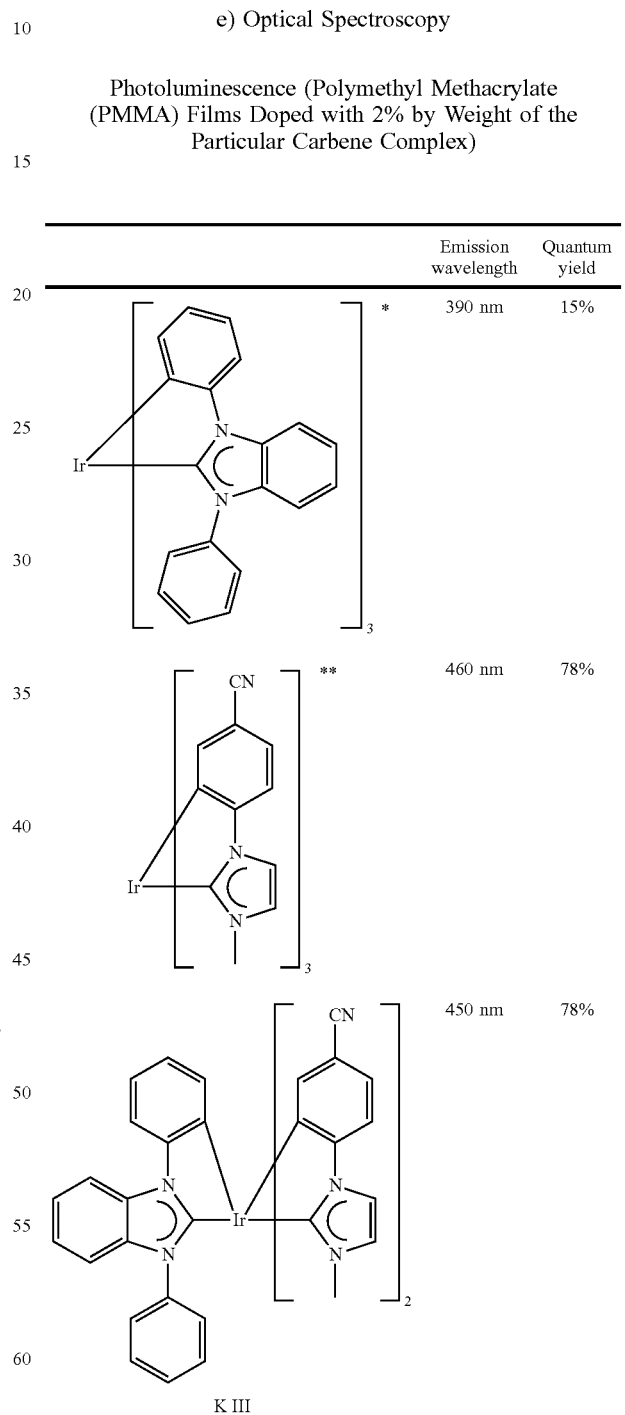

| | Emission wavelength | Quantum yield |
|---|---|---|
| * | 390 nm | 15% |
| ** | 460 nm | 78% |
| | 450 nm | 78% |

*for preparation, see Ir complex (7) in the application WO 05/019373
**for preparation, see German application 102004057072.8, filed on Nov. 25, 2004, title: "Verwendung von Übergangsmetall-Carbenkomplexen in organischen Licht-emitterenden Dioden (OLEDs)" [Use of transition metal-carbene complexes in organic light-emitting diodes(OLEDs)]

f) Production of an OLED

The ITO substrate used as the anode is first cleaned with commercial detergents for LCD production (Deconex® 20NS and neutralizer 25ORGAN-ACID®) and then in an acetone/isopropanol mixture in an ultrasound bath. To remove possible organic residues, the substrate is exposed to a continuous ozone flow in an ozone oven for a further 25 minutes. This treatment also improves the hole injection properties of the ITO.

Thereafter, the organic materials specified below are applied to the cleaned substrate by vapor deposition at a rate of approx. 2-3 nm/min at about $10^{-7}$ mbar. The hole conductor and exciton blocker applied to the substrate is Ir(d-pbic)$_3$ with a thickness of 20 nm.

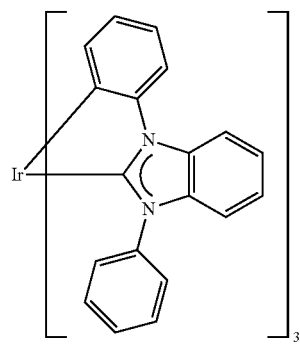

(for preparation, see Ir complex (7) in the application WO 05/019373).

Subsequently, a mixture of 30% by weight of the compound

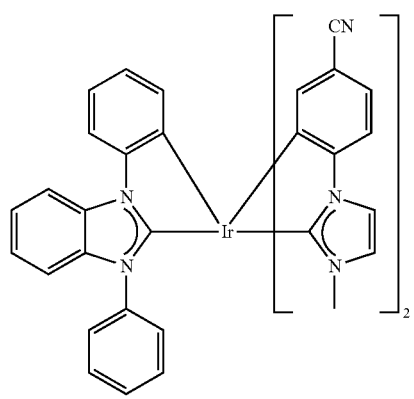

K III and 70% by weight of the compound

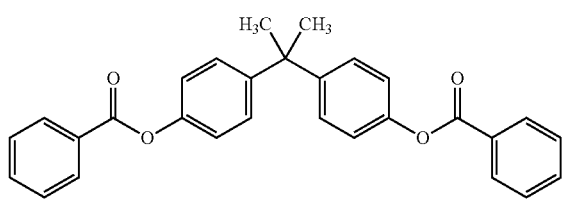 [SMILES: CC(C)(c1ccc(OC(=O)c2ccccc2)cc1)c1ccc(OC(=O)c2ccccc2)cc1]

(for preparation, see German application 102005014284.2, filed on: Mar. 24, 2005, title: "Verwendung von Verbindungen, welche aromatische oder heteroaromatische über Carbonyl-Gruppen enthaltende Gruppen verbundene Ringe enthalten, als Matrixmaterialien in organischen Leuchtdioden" [Use of compounds which comprise aromatic or heteroaromatic rings bonded via groups comprising carbonyl groups as matrix materials in organic light-emitting diodes]) is applied by vapor deposition in a thickness of 20 nm, the former compound functioning as an emitter, the latter as a matrix material.

Subsequently, the material

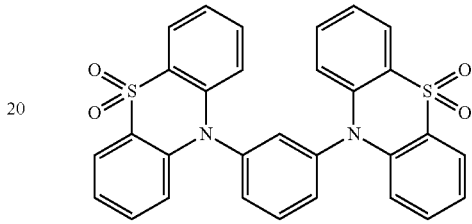

(for preparation, see German application 102004057073.6, filed on: Nov. 25, 2004, title: "Verwendung von Phenothiazin-5-oxiden und —S,S-dioxiden als Matrixmaterialien für organische Leuchtdioden" [Use of phenothiazine S-oxides and S,S-dioxides as matrix materials for organic light-emitting diodes])

is applied by vapor deposition with a thickness of 9 nm as an exciton and hole blocker.

Next, an electron transporter TPBI (1,3,5-tris(N-phenyl-benzylimidazol-2-yl)benzene) is applied by vapor deposition in a thickness of 40 nm, as are a 0.75 nm-thick lithium fluoride layer and finally a 110 nm-thick Al electrode.

To characterize the OLED, electroluminescence spectra are recorded at different currents and voltages. In addition, the current-voltage characteristic is measured in combination with the emitted light output. The light output can be converted to photometric parameters by calibration with a photometer.

For the OLED described, the following electrooptical data are obtained:

| | |
|---|---|
| Emission maximum | 456 nm |
| CIE(x, y) | 0.155; 0.12 |
| Photometric efficiency at 4 V | 9.6 cd/A |
| Power efficiency at 4 V | 7.5 lm/W |
| External quantum yield at 4 V | 9.7% |
| Luminance at 7 V | 1500 cd/m$^2$ |

The invention claimed is:

1. A heteroleptic carbene complex of the general formula (Ii) comprising two different carbene ligands (IIa) and (IIb),

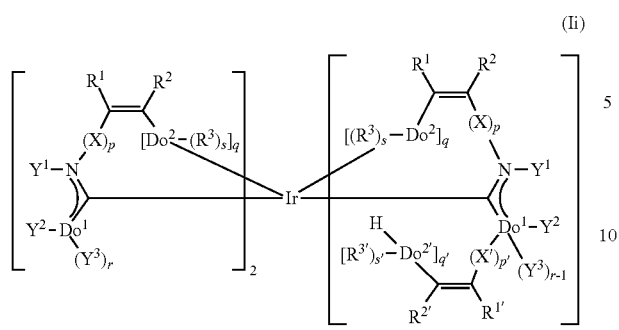

wherein the ligand (IIa)

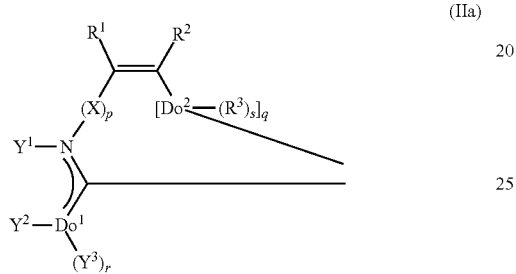

is

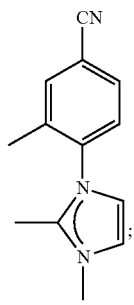 [SMILES: Cc1cc(C#N)ccc1N1C=CN(C)C1C]

and
wherein, in the carbene ligand (IIb)

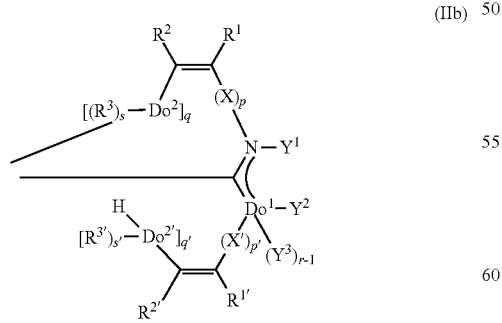

Do$^1$ is a donor atom selected from the group consisting of C, P, N and Si;
Do$^2$ is a donor atom selected from the group consisting of C, N, P, O and S;

r is 2 when Do$^1$ is C or Si, is 1 when Do$^1$ is N or P;
s is 2 when Do$^2$ is C, 1 when Do$^2$ is N or P, and are each 0 when Do$^2$ is O or S;
X is a spacer selected from the group consisting of silylene, alkylene, arylene, heteroarylene, alkynylene, alkenylene, NR$^{13}$, PR$^{14}$, BR$^{15}$, O, S, SO, SO$_2$, CO, CO—O, O—CO and (CR$^{16}$R$^{17}$)$_w$, where one or more nonadjacent (CR$^{16}$R$^{17}$) groups may be replaced by NR$^{13}$, PR$^{14}$, BR$^{15}$, O, S, SO, SO$_2$, CO, CO—O, or O—CO;
w is from 2 to 10;
R$^{13}$, R$^{14}$, R$^{15}$, R$^{16}$, and R$^{17}$ are each independently selected from the group consisting of H, alkyl, aryl, heteroaryl, alkenyl, and alkynyl;
p is 0 or 1;
q is 0 or 1;
p' is 0;
q' is 0;
Y$^1$ and Y$^2$ are each independently hydrogen, a carbon group selected from the group consisting of alkyl, aryl, heteroaryl, alkynyl and alkenyl groups, or together form a bridge between the donor atom Do$^1$ and the nitrogen atom N which has at least two atoms, of which at least one is a carbon atom;
R$^1$ and R$^2$ are each independently hydrogen, an alkyl, an aryl, a heteroaryl, an alkynyl, an alkenyl, or R$^1$ and R$^2$ together form a bridge having a total of from three to five atoms, of which 1 to 5 atoms may be heteroatoms and the remaining atoms are carbon atoms, so that the group

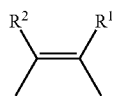

forms a five- to seven-membered ring which optionally—in addition to the double bond already present—may have one further double bond or—in the case of a six- or seven-membered ring—two further double bonds, and may optionally be substituted by alkyl or aryl groups and/or groups with donor or acceptor action, and may optionally comprise at least one heteroatom, and the five- to seven-membered ring may optionally be fused to one or more further rings;
Y$^1$ and R$^1$ or Y$^2$ and R$^{1'}$ may be bonded to one another via a bridge where the bridge is a group selected from the group consisting of alkylene, arylene, heteroarylene, alkynylene, alkenylene, NR$^{18}$, PR$^{19}$, BR$^{20}$, O, S, SO, SO$_2$, SiR$^{30}$R$^{31}$, CO, CO—O, O—CO and (CR$^{21}$R$^{22}$)$_x$, where one or more nonadjacent (CR$^{21}$R$^{22}$) groups may be replaced by NR$^{18}$, PR$^{19}$, BR$^{20}$, O, S, SO, SO$_2$, SiR$^{30}$R$^{31}$, CO, CO—O, or O—CO, where
x is from 2 to 10, and
R$^{18}$, R$^{19}$, R$^{20}$, R$^{21}$, R$^{22}$, R$^{30}$ and R$^{31}$ are each independently selected from the group consisting of H, alkyl, aryl, heteroaryl, alkenyl, and alkynyl;
R$^3$ is selected from the group consisting of hydrogen, an alkyl, aryl, heteroaryl, alkynyl and alkenyl radical;

$Y^3$ is a hydrogen, an alkyl, alkynyl, or alkenyl radical; and

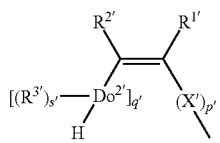

in the carbene ligand (IIb) has the structure

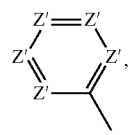

wherein one occurrence of $Z'$ in an o-position relative to the bonding site with $Do^1$ is CH, the other occurrence of $Z'$ in an o-position relative to the bonding site with $Do^1$ is $CR^{12'}$, each occurrence of $Z'$ in an m- or p-position relative to the bonding site with $Do^1$ is independently $CR^{12'}$ or N, provided 0 or only 1 $Z'$ is N, and $R^{12'}$ in the $Z'$ groups are each independently selected from the group consisting of H, an alkyl, aryl, heteroaryl, alkynyl, alkenyl radical and a radical with donor or acceptor action, where 2 $R^{12'}$ radicals optionally form a fused ring, wherein the fused ring may optionally comprise at least one heteroatom;

wherein, the aromatic base of the structure

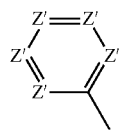

or one of the $R^{12'}$ radicals is optionally bonded to $Y^2$ via a bridge, wherein the bridge is selected from the group consisting of alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, or O—CO, where x is from 2 to 10, and $R^{18}$, $R^{19}$, $R^{20}$, $R^{21}$, $R^{22}$, $R^{30}$, $R^{31}$ are each independently selected from the group consisting of H, alkyl, aryl, heteroaryl, alkenyl, and alkynyl.

2. An organic light-emitting diode comprising at least one heteroleptic carbene complex according to claim 1.

3. A device selected from the group consisting of stationary visual display units and mobile visual display units comprising at least one organic light-emitting diode according to claim 2.

4. A light-emitting layer comprising at least one heteroleptic carbene complex according to claim 1.

5. An organic light-emitting diode comprising an anode and a cathode and at least one light-emitting layer according to claim 4 between the anode and the cathode.

6. A device selected from the group consisting of stationary visual display units and mobile visual display units comprising at least one organic light-emitting diode according to claim 5.

7. The organic light-emitting diode according to claim 5, wherein the organic light-emitting diode further comprises a hole transporting layer between the anode and the light-emitting layer, wherein the hole transporting layer comprises a carbene complex.

8. The organic light-emitting diode according to claim 7, wherein the carbene complex is a homoleptic carbene complex.

9. An organic light-emitting diode comprising an anode and a cathode and at least one light-emitting layer between the anode and the cathode, wherein the light-emitting layer comprises

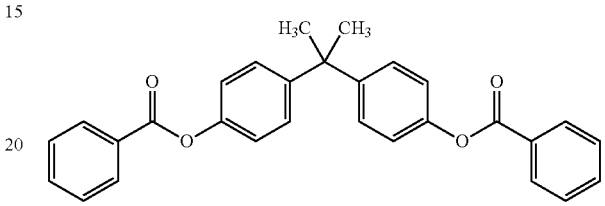

and at least one heteroleptic carbene complex of the general formula (Ii) comprising two different carbene ligands (IIa) and (IIb),

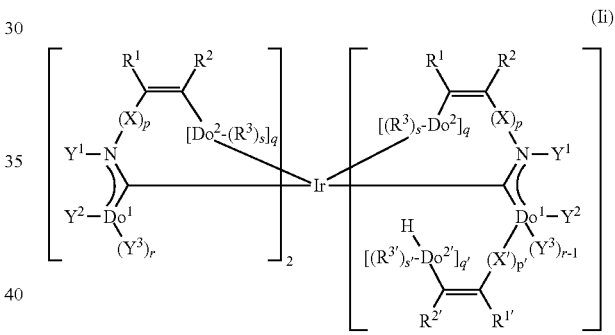

wherein, in the ligand (IIa)

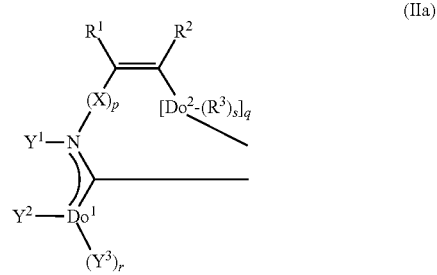

$Do^1$ is a donor atom selected from the group consisting of C, P, N, O, S and Si;

$Do^2$ is a donor atom selected from the group consisting of C, N, P, O and S;

r is 2 when $Do^1$ is C or Si, is 1 when $Do^1$ is N or P, and is 0 when $Do^1$ is O or S;

s is 2 when $Do^2$ is C, 1 when $Do^2$ is N or P, and is 0 when $Do^2$ is O or S;

X is a spacer selected from the group consisting of silylene, alkylene, arylene, heteroarylene, alkynylene, alkenylene, $NR^{13}$, $PR^{14}$, $BR^{15}$, O, S, SO, $SO_2$, CO, CO—O, O—CO and $(CR^{16}R^{17})_w$, where one or more nonadjacent $(CR^{16}R^{17})$ groups may be replaced by $NR^{13}$, $PR^{14}$, $BR^{15}$, O, S, SO, $SO_2$, CO, CO—O, or O—CO;

w is from 2 to 10;

$R^{13}$, $R^{14}$, $R^{15}$, $R^{16}$, and $R^{17}$ are each independently selected from the group consisting of H, alkyl, aryl, heteroaryl, alkenyl, and alkynyl;

p is 0 or 1;

q is 0 or 1;

$Y^1$ and $Y^2$ are each independently hydrogen, a carbon group selected from the group consisting of alkyl, aryl, heteroaryl, alkynyl and alkenyl groups, or together form a bridge between the donor atom $Do^1$ and the nitrogen atom N which has at least two atoms, of which at least one is a carbon atom;

$R^1$ and $R^2$ are each independently hydrogen, an alkyl, an aryl, a heteroaryl, an alkynyl, an alkenyl, or $R^1$ and $R^2$ together form a bridge having a total of from three to five atoms, of which 1 to 5 atoms may be heteroatoms and the remaining atoms are carbon atoms, so that the group

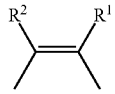

forms a five- to seven-membered ring which optionally—in addition to the double bond already present—may have one further double bond or—in the case of a six- or seven-membered ring—two further double bonds, and may optionally be substituted by alkyl or aryl groups and/or groups with donor or acceptor action, and may optionally comprise at least one heteroatom, and the five- to seven-membered ring may optionally be fused to one or more further rings;

$Y^1$ and $R^1$ may be bonded to one another via a bridge, where the bridge is a group selected from the group consisting of alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, or O—CO, where x is from 2 to 10;

$R^{18}$, $R^{19}$, $R^{20}$, $R^{21}$, $R^{22}$, $R^{30}$ and $R^{31}$ are each independently selected from the group consisting of H, alkyl, aryl, heteroaryl, alkenyl, and alkynyl;

$R^3$ is selected from the group consisting of hydrogen, an alkyl, aryl, heteroaryl, alkynyl and alkenyl radical; and $Y^3$ is an alkyl radical;

wherein, in the carbene ligand (IIb)

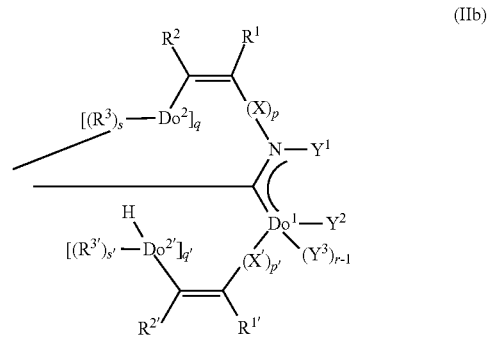

$Do^1$ is a donor atom selected from the group consisting of C, P, N and Si;

$Do^2$ is a donor atom selected from the group consisting of C, N, P, O and S;

r is 2 when $Do^1$ is C or Si, is 1 when $Do^1$ is N or P;

s is 2 when $Do^2$ is C, 1 when $Do^2$ is N or P, and are each 0 when $Do^2$ is O or S;

X is a spacer selected from the group consisting of silylene, alkylene, arylene, heteroarylene, alkynylene, alkenylene, $NR^{13}$, $RP^{14}$, $BR^{15}$, O, S, SO, $SO_2$, CO, CO—O, O—CO and $(CR^{16}R^{17})$, where one or more nonadjacent $(CR^{16}R^{17})$ groups may be replaced by $NR^{13}$, $PR^{14}$, $BR^{15}$, O, S, SO, $SO_2$, CO, CO—O, or O—CO;

w is from 2 to 10;

$R^{13}$, $R^{14}$, $R^{15}$, $R^{16}$, and $R^{17}$ are each independently selected from the group consisting of H, alkyl, aryl, heteroaryl, alkenyl, and alkynyl;

p is 0 or 1;

q is 0 or 1;

p' is 0;

q' is 0;

$Y^1$ and $Y^2$ are each independently hydrogen, a carbon group selected from the group consisting of alkyl, aryl, heteroaryl, alkynyl and alkenyl groups, or together form a bridge between the donor atom $Do^1$ and the nitrogen atom N which has at least two atoms, of which at least one is a carbon atom;

$R^1$ and $R^2$ are each independently hydrogen, an alkyl, an aryl, a heteroaryl, an alkynyl, an alkenyl, or $R^1$ and $R^2$ together form a bridge having a total of from three to five atoms, of which 1 to 5 atoms may be heteroatoms and the remaining atoms are carbon atoms, so that the group

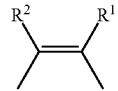

forms a five- to seven-membered ring which optionally—in addition to the double bond already present—may have one further double bond or—in the case of a six- or seven-membered ring—two further double bonds, and may optionally be substituted by alkyl or aryl groups and/or groups with donor or acceptor action, and may optionally comprise at least one heteroatom, and the five- to seven-membered ring may optionally be fused to one or more further rings;

$Y^1$ and $R^1$ or $Y^2$ and $R^{1'}$ may be bonded to one another via a bridge where the bridge is a group selected from the group consisting of alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, or O—CO, where x is from 2 to 10, and $R^{18}$, $R^{19}$, $R^{20}$, $R^{21}$, $R^{22}$, $R^{30}$ and $R^{31}$ are each independently selected from the group consisting of H, alkyl, aryl, heteroaryl, alkenyl, and alkynyl;

$R^3$ is selected from the group consisting of hydrogen, an alkyl, aryl, heteroaryl, alkynyl and alkenyl radical;

$Y^3$ is a hydrogen, an alkyl, alkynyl, or alkenyl radical; and in the carbene ligand (IIb) has the structure wherein one occurrence of Z' in an o-position relative to the bonding site with $Do^1$ is CH, the other occurrence of Z' in an o-position relative to the bonding site with $Do^1$ is $CR^{12'}$, each occurrence of Z' in an m- or p-position relative to the bonding site with $Do^1$ is independently $CR^{12'}$ or N, provided 0 or only 1 Z' is N, and $R^{12'}$ in the Z' groups are each independently selected from the group consisting of H, an alkyl, aryl, heteroaryl, alkynyl, alkenyl radical and a radical with donor or acceptor action, wherein 2 $R^{12'}$ radicals optionally form a fused ring, wherein the fused ring may optionally comprise at least one heteroatom;

wherein, the aromatic base of the structure or one of the $R^{12'}$ radicals is optionally bonded to $Y^2$ via a bridge, wherein the bridge is selected from the group consisting of alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, or O—CO, where x is from 2 to 10; and $R^{18}$, $R^{19}$, $R^{20}$, $R^{21}$, $R^{22}$, $R^{30}$, $R^{31}$ are each independently selected from the group consisting of H, alkyl, aryl, heteroaryl, alkenyl, and alkynyl.

10. A device selected from the group consisting of stationary visual display units and mobile visual display units comprising at least one organic light-emitting diode according to claim 9.

11. The organic light-emitting diode according to claim 9, wherein the organic light-emitting diode further comprises a hole transporting layer between the anode and the light-emitting layer, wherein the hole transporting layer comprises a carbene complex.

12. The organic light-emitting diode according to claim 11, wherein the carbene complex is a homoleptic carbene complex.

13. A light-emitting layer comprising and at least one heteroleptic carbene complex of the general formula (Ii) comprising two different carbene ligands (IIa) and (IIb), (Ii)

wherein, in the ligand (IIa)

(IIa)

$Do^1$ is a donor atom selected from the group consisting of C, P, N, O, S and Si;

$Do^2$ is a donor atom selected from the group consisting of C, N, P, O and S;

r is 2 when $Do^1$ is C or Si, is 1 when $Do^1$ is N or P, and is 0 when $Do^1$ is O or S;

s is 2 when Do² is C, 1 when Do² is N or P, and is 0 when Do² is O or S;

X is a spacer selected from the group consisting of silylene, alkylene, arylene, heteroarylene, alkynylene, alkenylene, NR¹³, PR¹⁴, BR¹⁵, O, S, SO, SO₂, CO, CO—O, O—CO and (CR¹⁶R¹⁷)$_w$, where one or more nonadjacent (CR¹⁶R¹⁷) groups may be replaced by NR¹³, PR¹⁴, BR¹⁵, O, S, SO, SO₂, CO, CO—O, or O—CO;

w is from 2 to 10;

R¹³, R¹⁴, R¹⁵, R¹⁶ and R¹⁷ are each independently selected from the group consisting of H, alkyl, aryl, heteroaryl, alkenyl, and alkynyl;

p is 0 or 1;

q is 0 or 1;

Y¹ and Y² are each independently hydrogen, a carbon group selected from the group consisting of alkyl, aryl, heteroaryl, alkynyl and alkenyl groups, or together form a bridge between the donor atom Do¹ and the nitrogen atom N which has at least two atoms, of which at least one is a carbon atom;

R¹ and R² are each independently hydrogen, an alkyl, an aryl, a heteroaryl, an alkynyl, an alkenyl, or R¹ and R² together form a bridge having a total of from three to five atoms, of which 1 to 5 atoms may be heteroatoms and the remaining atoms are carbon atoms, so that the group

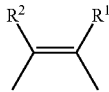

forms a five- to seven-membered ring which optionally—in addition to the double bond already present—may have one further double bond or—in the case of a six- or seven-membered ring—two further double bonds, and may optionally be substituted by alkyl or aryl groups and/or groups with donor or acceptor action, and may optionally comprise at least one heteroatom, and the five- to seven-membered ring may optionally be fused to one or more further rings;

Y¹ and R¹ may be bonded to one another via a bridge, where the bridge is a group selected from the group consisting of alkylene, arylene, heteroarylene, alkynylene, alkenylene, NR¹⁸, PR¹⁹, BR²⁰, O, S, SO, SO₂, SiR³⁰R³¹, CO, CO—O, O—CO and (CR²¹R²²)$_x$, where one or more nonadjacent (CR²¹R²²) groups may be replaced by NR¹⁸, PR¹⁹, BR²⁰, O, S, SO, SO₂, SiR³⁰R³¹, CO, CO—O, or O—CO, where x is from 2 to 10;

R¹⁸, R¹⁹, R²⁰, R²¹, R²², R³⁰ and R³¹ are each independently selected from the group consisting of H, alkyl, aryl, heteroaryl, alkenyl, and alkynyl;

R³ is selected from the group consisting of hydrogen, an alkyl, aryl, heteroaryl, alkynyl and alkenyl radical; and Y³ is an alkyl radical;

wherein, in the carbene ligand (IIb)

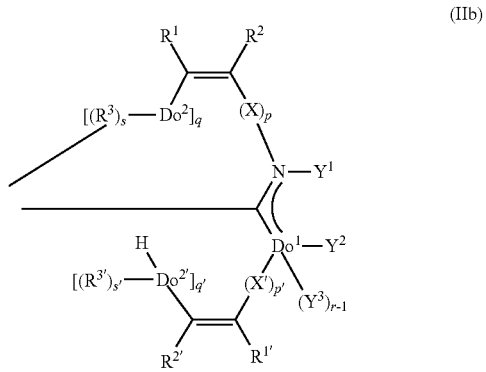

Do¹ is a donor atom selected from the group consisting of C, P, N and Si;

Do² is a donor atom selected from the group consisting of C, N, P, O and S;

r is 2 when Do¹ is C or Si, is 1 when Do¹ is N or P;

s is 2 when Do² is C, 1 when Do² is N or P, and are each 0 when Do² is O or S;

X is a spacer selected from the group consisting of silylene, alkylene, arylene, heteroarylene, alkynylene, alkenylene, NR¹³, PR¹⁴, BR¹⁵, O, S, SO, SO₂, CO, CO—O, O—CO and (CR¹⁶R¹⁷)$_w$, where one or more nonadjacent (CR¹⁶R¹⁷) groups may be replaced by NR¹³, PR¹⁴, BR¹⁵, O, S, SO, SO₂, CO, CO—O, or O—CO;

w is from 2 to 10;

R¹³, R¹⁴, R¹⁵, R¹⁶, and R¹⁷ are each independently selected from the group consisting of H, alkyl, aryl, heteroaryl, alkenyl, and alkynyl;

p is 0 or 1;

q is 0 or 1;

p' is 0;

q' is 0;

Y¹ and Y² are each independently hydrogen, a carbon group selected from the group consisting of alkyl, aryl, heteroaryl, alkynyl and alkenyl groups, or together form a bridge between the donor atom Do¹ and the nitrogen atom N which has at least two atoms, of which at least one is a carbon atom;

R¹ and R² are each independently hydrogen, an alkyl, an aryl, a heteroaryl, an alkynyl, an alkenyl, or R¹ and R² together form a bridge having a total of from three to five atoms, of which 1 to 5 atoms may be heteroatoms and the remaining atoms are carbon atoms, so that the group

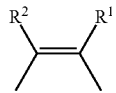

forms a five- to seven-membered ring which optionally—in addition to the double bond already present—may have one further double bond or—in the case of a six- or seven-membered ring—two further double bonds, and may optionally be substituted by alkyl or aryl groups and/or groups with donor or acceptor action, and may optionally comprise at least one heteroatom, and the five- to seven-membered ring may optionally be fused to one or more further rings;

$Y^1$ and $R^1$ or $Y^2$ and $R^{1'}$ may be bonded to one another via a bridge where the bridge is a group selected from the group consisting of alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, or O—CO, where x is from 2 to 10, and $R^{18}$, $R^{19}$, $R^{20}$, $R^{21}$, $R^{22}$, $R^{30}$ and $R^{31}$ are each independently selected from the group consisting of H, alkyl, aryl, heteroaryl, alkenyl, and alkynyl;

$R^3$ is selected from the group consisting of hydrogen, an alkyl, aryl, heteroaryl, alkynyl and alkenyl radical;

$Y^3$ is a hydrogen, an alkyl, alkynyl, or alkenyl radical; and

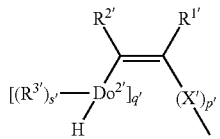

in the carbene ligand (IIb) has the structure

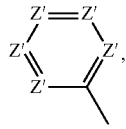

wherein one occurrence of Z' in an o-position relative to the bonding site with $Do^1$ is CH, the other occurrence of Z' in an o-position relative to the bonding site with $Do^1$ is $CR^{12'}$, each occurrence of Z' in an m- or p-position relative to the bonding site with $Do^1$ is independently $CR^{12'}$ or N, provided 0 or only 1 Z' is N, and $R^{12'}$ in the Z' groups are each independently selected from the group consisting of H, an alkyl, aryl, heteroaryl, alkynyl, alkenyl radical and a radical with donor or acceptor action, wherein 2 $R^{12'}$ radicals optionally form a fused ring, wherein the fused ring may optionally comprise at least one heteroatom;

wherein, the aromatic base of the structure

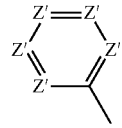

or one of the $R^{12'}$ radicals is optionally bonded to $Y^2$ via a bridge, wherein the bridge is selected from the group consisting of alkylene, arylene, heteroarylene, alkynylene, alkenylene, $NR^{18}$, $PR^{19}$, $BR^{20}$, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, or O—CO, where x is from 2 to 10; and $R^{18}$, $R^{19}$, $R^{20}$, $R^{21}$, $R^{22}$, $R^{30}$, $R^{31}$ are each independently selected from the group consisting of H, alkyl, aryl, heteroaryl, alkenyl, and alkynyl.

14. An organic light-emitting diode comprising an anode and a cathode and at least one light-emitting layer according to claim 13 between the anode and the cathode.

15. A device selected from the group consisting of stationary visual display units and mobile visual display units comprising at least one organic light-emitting diode according to claim 14.

16. The organic light-emitting diode according to claim 14, wherein the organic light-emitting diode further comprises a hole transporting layer between the anode and the light-emitting layer, wherein the hole transporting layer comprises a carbene complex.

17. The organic light-emitting diode according to claim 16, wherein the carbene complex is a homoleptic carbene complex.

* * * * *